US006630618B2

(12) United States Patent
Baker et al.

(10) Patent No.: US 6,630,618 B2
(45) Date of Patent: Oct. 7, 2003

(54) TRANSGENIC PLANTS HAVING NON-PATHOGEN INDUCED SYSTEMIC ACQUIRED RESISTANCE (SAR)

(75) Inventors: Barbara J. Baker, Berkeley, CA (US); Savithramma Puttaswamy Dinesh-Kumar, New Haven, CT (US)

(73) Assignees: The United States of America as represented by the Secretary of Agriculture, Washington, DC (US); Regents of the University of California, Oakland, CA (US)

( * ) Notice: Subject to any disclaimer, the term of this patent is extended or adjusted under 35 U.S.C. 154(b) by 8 days.

(21) Appl. No.: 09/813,742

(22) Filed: Mar. 21, 2001

(65) Prior Publication Data

US 2002/0004944 A1 Jan. 10, 2002

Related U.S. Application Data

(60) Provisional application No. 60/191,027, filed on Mar. 21, 2000.

(51) Int. Cl.[7] .............................. A01H 5/00; A01H 5/10; C12N 15/82
(52) U.S. Cl. ........................ 800/301; 800/317; 800/279
(58) Field of Search ................................. 800/279, 301, 800/317.3, 317.4, 317.1; 435/419, 468

(56) References Cited

U.S. PATENT DOCUMENTS 5,571,706 A * 11/1996 Baker et al.

FOREIGN PATENT DOCUMENTS

| WO | WO 95/28423 A1 | 10/1995 |
| WO | WO 98/02545 A3 | 1/1998 |

OTHER PUBLICATIONS

Fluhr et al, 2001, Plant Physiol. 127:1367–1374.*
Dinesh–Kumar, 2000, Proc. Natl. Acad. Sci USA 97:14789–14794.*
Anderson, P. et al., Inactivation of the Flax Rust Resistance Gene M Associated with Loss of a Repeated Unit Within the Leucine–Rich Repeat Coding Region, *Plant Cell*, 1997, pp. 641–651, vol. 9.
Baker, B. et al., Signaling in Plant–Microbe Interactions, *Science*, 1997, pp. 726–733, vol. 276.
Bent, A. et al., RPS2 of *Arabidopsis thaliana*: A Leucine–Rich Repeat Class of Plant Disease Resistance Genes, *Science*, 1994, pp. 1856–1860, vol. 265.
Botella, M. et al., Three Genes of the Arabidopsis RPPI Complex Resistance Locus Recognize Distinct*Peronospora parasitica* Avirulence Determinants, *Plant Cell*, 1998, pp. 1847–1860, vol. 10.
CAI, D. et al., Positional Cloning of a Gene for Nematode Resistance in Sugar Beet, *Science*, 1997, pp. 832–834, vol. 275.

CAO, H. et al., Generation of Broad–Spectrum Disease Resistance by Overexpression of an Essential Regulatory Gene in Systemic Acquired Resistance, *Proc Natl Acad Sci USA*, 1998, pp. 6531–6536, vol. 95.
Dixon, M. et al., The Tomato Cf–5 Disease Resistance Gene and Six Homologs Show Pronounced Allelic Variation in Leucine–Rich Repeat Copy Number, *Plant Cell*, 1998, pp. 1915–1926, vol. 10.
Grant, M. et al., Structure of the *Arabidopsis RPM1*, Gene Enabling Dual Specificity Disease Resistance, *Science*, 1995, pp. 843–846, vol. 269.
Johal, G. and Briggs, S., Reductase Activity Encoded by the HM1 Disease Resistance Gene in Maize, *Science*, 1992, pp. 985–987, vol. 258.
Lawrence, G. et al., The L6 Gene for Flax Rust Resistance is Related to the Arabidopsis Bacterial Resistance Gene RPS2 and the Tobacco Viral Resistance Gene N, *Plant Cell*, 1995–1206, pp. 1195, vol. 7.
Martin, G. et al., Map–Based Cloning of Protein Kinase Gene Conferring Disease Resistance in Tomato, *Science*, 1993, pp. 1432–1436, vol. 262.
Ori, N. et al., The I2C Family from the Wilt Disease Resistance Locus I2C Belongs to the Nucleotide Binding, Leucine–Rich Repeat Superfamily of Plant Resistance Genes, *Plant Cell*, 1997, pp. 521–532, vol. 9.
Parker, J. et al., The Arabidopsis Downy Mildew Resistance Gene RPP5 Shares Similarity to the Toll and Interleukin–1 Receptors with N and L6, *Plant Cell*, 1997, pp. 879–894, vol. 9.
Song, W. et al., A Receptor Kinase–Like Protein Encoded by the Rice Disease Resistance Gene, Xa21, *Science*, 1995, pp. 1804–1806, vol. 270.
Jones, D. et al., Isolation of the Tomato Cf–9 Gene for Resistance to *Cladosporium fulvum* by Transposon Tagging, *Science*, 1994, pp. 789–793, vol. 266.
Whitham, S. et al., The Product of the Tobacco Mosaic Virus Resistance Gene N: Similarity to Toll and the Interleukin–1 Receptor, *Cell*, 1994, pp. 1101–1115, vol. 78.

* cited by examiner

*Primary Examiner*—Amy J. Nelson
*Assistant Examiner*—Anne Kubelik
(74) *Attorney, Agent, or Firm*—Alston & Bird LLP

(57) ABSTRACT

The present invention discloses the production of transgenic plants that exhibit a systemic acquired resistance (SAR) response even in the absence of an infecting pathogen. The transgenic plants are produced by a method comprising obtaining a plant having a first nucleic acid molecule encoding one or more protein products of the N gene sufficient to confer resistance to a phytopathogen and introducing into the genome of said plant a second nucleic acid molecule encoding the TIR domain of the N gene, wherein co-expression of the first and second nucleic acid molecules is sufficient to produce a systemic acquired resistance response in the plant in the absence of an infecting pathogen. The invention encompasses such plants, methods and biological molecules useful for producing the plants, and methods for increasing the disease resistance of plants.

18 Claims, 5 Drawing Sheets

```
            1                                                          50
     M  MSYLRDVATA VALLLDNLCC GRPNLNNDNE DTTQQTDSTS PVVDPSSSSQ
    16  MSYLREVATA VALLLPFILL NKFWRPNSKD SIVNDDD...  ..........
     N  ---------- ---------- ---------- ---------- ----------
  rpp5  ---------- ---------- ----MDSSFF LVLVAAATGF FMLFRKFRFH
  rpp1  ---------- ---------- ---------- ---------- ----------
  CONS  ---------- ---------- ---------- ---------- ----------

51                                                         100
     M  SMDSTSVVDA ISDSTNPSAS FPSVEYDVFL SFRGPDTRYQ ITDILYRFLC
    16  ..DSTSEVDA ISDSTNPSGS FPSVEYEVFL SFRGPDTREQ FTDFLYQSLR
     N  ---------- ----MASSSS SSRWSYDVFL SFRCEDTRKT FTSHLYEVLN
  rpp5  ---------- ----MAASSS SGRRRYDVFP SFSGVDVRKT FLSHLLKALD
  rpp1  QDNKESNSSS LSRPTAATSV SRNWKHDVFP SFHGADVRRT FLSHILESFR
  CONS  -----S---- -S--TA-SSS S----YDVFL SFRG-DTR-T FTSHLY--L-

101                                                        150
     M  RSKIHTFKDD DELHKGEEIK VNLLRAIDQS KIYVPIISRG YADSKWCLME
    16  RYKIHTFRDD DELLKGKEIG PNLLRAIDQS KIYVPIISSG YADSKWCLME
     N  DKGIKTFQDD KRLEYGATIP GELCKAIEES QFAIVVFSEN YATSRWCLNE
  rpp5  GKSINTF.ID HGIERSRTIA PELISAYREA RISIVIFSKN YASSTWCLNE
  rpp1  RKGIDTF.ID NNIERSKSIG PELKEAIKGS KIAIVLLSRK YASSSWCLDE
  CONS  RK-I-TF-DD --LE-G---I- PEL--AI--S KI-IVI-S-- YA-S-WCL-E 151                                                        200
     M  LAKIVRHQKL DTRQIIIPIF YMVDPKDVRH QTGPYRKAFQ KHS....TRY
    16  LAEIVRRQEE DPRRIILPIF YMVDPSDVRH QTGCYKKAFR KHA....NKF
     N  LVKIMECKT. RFKQTVIPIF YDVDPSHVRN QKESFAKAFE E..HETKYKD
  rpp5  LVEIHKCFN. DLGQMVIPVF YDVDPSEVRK QTGEFGKVFE KTCEVSKDKQ
  rpp1  LAEIMKCRE. VLGQIVMTIF YEVEPTDIKK QTGEFGKAFT KTCR.GKTK.
  CONS  LAEI--C--- D--QIVIPIF Y-VDPSDVR- QTG-F-KAF- K-----K-K-

201                                                        250
     M  DEMT------ ---------- ---------- ---------- ----------
    16  DGQTIQNWKD ALKKVGDLK- ---------- ---------- ----------
     N  DVEGIQRWRI ALNEAANLKG SCDNRDKTDA ---------- ----------
  rpp5  PGDQKQRWVQ ALTDIANIAG EDLLNGPNEA HMVEKISNDV SNKLITRSKC
  rpp1  ..EHIERWRK ALEDVATIAG YASHKWSNEA ---------- ----------
  CONS  D---IQRW-- AL---A---G ---------A ---------- ----------
```

FIG. 1.

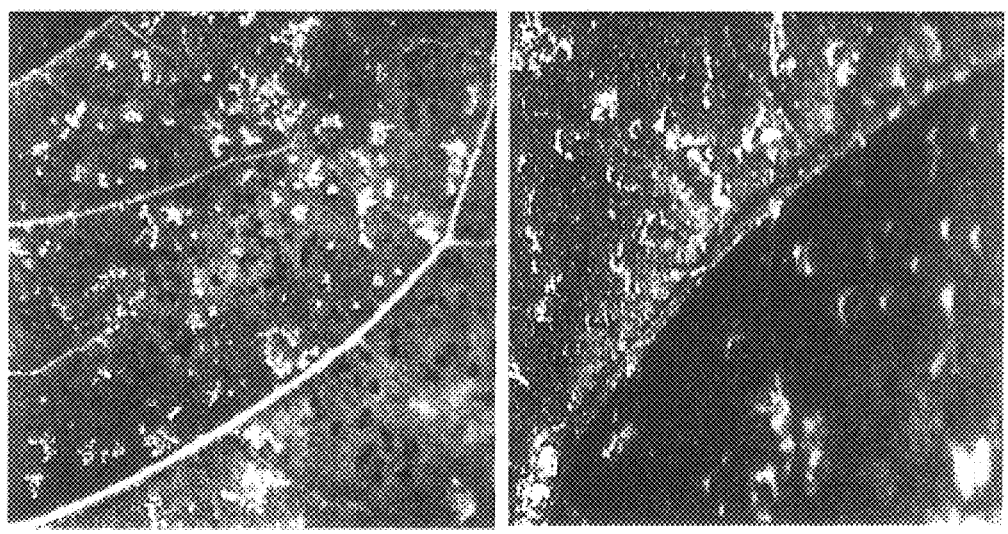
Constitutive HR phenotype in
TIR over expressing plants in
the absence of TMV
FIG. 3.

PVX and TRV replication
is reduced in TIR-*NN* plants
showing constitutive HR

SEQUENCE LISTING

```
<160> NUMBER OF SEQ ID NOS: 11

<210> SEQ ID NO 1
<211> LENGTH: 12286
<212> TYPE: DNA
<213> ORGANISM: Nicotiana glutinosa

<400> SEQUENCE: 1
gatcttattc taattatatg acatttgcaa ctgtgaaggc aagaatttct tactctataa      60 tttttttaatt aaatatctaa tctaaaattt ctatagtaaa attgtgattt tgtgctcata    120
```

-continued

```
ttctcatatt tttcaatgtc tttgtttttc tttcttgttt tttatttact ttagggagga      180
gggcacacag ctcctgagta caaacgtgaa gagtgttttc atatgtttaa agatggata       240 actcaacaac ctttgtaaac atgtaacccc atcgaagatt aatttattaa atagccatta      300
ttaagcatct gtcttctttt ctttccgatt tttatgtgtg agggtgcaaa aattaactgt      360
aaaaatagta cgggctagcc agttttcgga ctaatcattc aaaatagtca acgtttgtca      420
agtcattgaa aaaatccgc tattttgctg caacagaaac cgtccagcat atatactgga       480
gttgggtgca catgtgtatg tatttccagt acattatgct ggaactccaa cacgcggaaa      540
gttccagcat aatatactgg agattcgagc acctgtgtaa aacttccag aatattatac       600 tggaccgata tagtttgctg gaaatccagt atattatgct ggagttctag tatatttatg      660
ctggaactcc attatattat cctggagttc cagtatactt atgctggaac tccagtataa      720
tatgctggag tttcactata cttatgctgg aactctagta taatatactg gaatattttc      780
cggatcttga acaatgtgtt cgttcaaatt tatctttaca tgaaaagtga ctaaatttta      840
attacttttg aaagtgtgac tatttttgaa tgagcacttg taaatctggt tattttttgaa     900 tttctcccga attaacttag tctaacaata tcttgttctg actggaaaat tcagtctaat      960
taattactgc attaactatc tcttcttctc tttgtgaatt ttttttttttt ttttataaca     1020 aatatgagat aatataaaaa cctctagttc ttctttgaaa aacaggtgag attccaatta     1080
aaacaaaatg ccattcttga acgattttga cagggctttt gcatctatat ccactttttg     1140
ggtcatattt taatttatac ccgctttgca aaaaattac aagcgtatcc actttttcgca     1200 taaacttcag gcttacgggt ctggagtagc aaaggcaatc acacaaaggt tcagcattct     1260 aggcttttttc gaaaacttca gcagaatgct gaagttattt agttcatttg taaaaacttc     1320
agcactaaat aagctgaagt tttgtcctgg attaaaataat tttgtcataa agcttttttca    1380 ataacttcag cagaagatgc tgaagttatt tagttcattt ataaaaactc cagcactaaa     1440
taagctgaag ttttttcttg aattaattag ttttgtcata aagcttttc aaaaaacttc       1500 agtgctgaag ttatttagtt cgttttaaa atcttcagca gaagatggtg aagttattaa      1560
gttcatttgt aaaaacttca gcatcagata agctgaagtt ttgtcctgga ttcattagtt     1620
ttgcagtaaa gcttttcaa aaacttcagc agaagatgct gaagttattt agttcatttg     1680
taaaaacttt agcactaaat atgctgaagt tttgcacagg tattagaaag gtggcgcctg     1740
aaattgtaaa aattaagata tatattaaat aatttaaaaa taaaggtata aattaaatga     1800
gagcgatcaa ataaggcgcc tgcgcaattt ttgatgtcaa ttaggtagca tcaagttaat     1860
tttgcacaat ttttgcgttt ctctatttag attgtttgaa aaaatgacaa ctttaataaa     1920
ttgccgaaat aataaaaaaa taaacaagtt gacagttacc tctttctcct cccgtacaac     1980
cttttcacca ccaccccctcc atgtccatga tttgttggtc cctaaagttt aaataataat     2040
aaataaataa ataaaaattg taattaaaat ttagagatca actttggtcg ttaaatatat     2100
attattaaaa tattataccg accgaagttg gtcggtattt tatttatcct aaatatttgg     2160
ttcttttaac ttagtgacca acgttggtcg ctaaattaaa aggaccacca atatagcgac     2220
caatccattt tggacgcgtt ttggtcggta tattgtgata agcgaccaac tttggtcgct     2280
atttgtggtc tcttttttgcc ggatttctag cagtgtgtac acgcaaatcg aaaaggataa     2340
aatgagattt ttaaggctaa cgagtgcaga attaaatttt aaaacgtaag tttaggtcat     2400
cacatattat gtgattttta aaaaaatgat cttcatatag aatacacacg taacacgctt     2460
```

```
gcccaaaaac tattagaaca aaataagtaa cggctatttt taaaccttca atccgtagca    2520
gcccactaat ccctggctcc aatttttcttc aataataagt tgtatgcaga aggaaaaaga   2580
ttgttcctag aagttgtatg cgatactaaa caccttcccc ctgttatttt tctgtctgtt    2640
ttctttaaag caacgaatcc tgtgccttga ttcttttctt gtttcctgtg ttagttataa    2700
gtttcaataa tgaaaaataa tatattatat tgggcgtagg atcacaaggg attcaagaag    2760
caacactagt cgggaataga taaggaaca taatcaataa tcagcatgga aaggaagaa      2820
gtagcgaaaa ttcggcaaga ataatcaatt taattaatta cagtagctaa ttcttatata    2880
ttaagtttct gagaaaagta acatttcttc acatttatgg acctacattt gttgtcactt    2940
tctatctgcg caaagaaaaa taagaccata gtactgcttt tggttagtac aactgttgac    3000
aaagaaaatt actgggatat tacccttcgt tttctttgta gctttatta tcggcttgta     3060
cttttagttg ttccttgtga acatattact gttgaatttg gtgcagggag ggtgggtggt    3120
ctttgaagga attacctact tcccttctat tacagtgcaa agaaaaccct ataacaataa    3180
taattctaat caactggagt aaacattaag atgaagcttc acaaaaaaat cctacaattt    3240
actttctatt aggagtagtc ggtggcggat ttaggatttt gcgaatatga gtgcactatt    3300
acgaagaggc gaatctagga tataaatttt acaggtttaa cgtttggttc ttactattgc    3360
acccattaca attttgaaat tataagttca aaattattat tttttaattg taattttctt    3420
atatctatt ccatactccg tacttaaaat attgggatca gtttaaccca atagcataca     3480
ctgcattatg cactagttta atatgcaaat tttatttaat catataagat ttttcggtga    3540
caaataacaa ataggaattt taatatgtga aaatttaaaa agaataaatc aaaagaaag    3600
aaagaaagaa aagaaatgt atttaattaa tacgcaccaa gtgatgccta gttttagaaa     3660
agaaaaaata acaataagat tgtcatagga aaaggattg aaaggtcgac cagataatt      3720
ttttttttt ttttttacca gaatgatatg ttccacaata tattgtacaa ttttgtcgaa     3780
actttataat aactttctta acgttaataa attgggaaca agtttacgat taaatttcac    3840
atgtgatcat tcaactttgt gtttattatc caacaaaaat gaaaatatt tgctagatg     3900
aagactttgt catcctcggt agaaaactaa aatagaaaaa gaattcaatc aatggagacc    3960
tttttctctt tggagcaata attcaattca attgggaagg aatttcctac tcccttctat    4020
taaagttcaa agaaaaccca ataattcctt ttattgcatt aagaagaatt ttcctactag    4080
tgtatatcag ttgactagga caccaataat tctatggagt agagcccatc tcacacaaac    4140
tttttccaat agcaatataa ctcttatctc ttctaatata tataaaaatt tgttgaaaat    4200
atcatctatt attttcttac cacaatcaca attttttcac atacagtttc ttattctttt   4260
cagagaatta acgttgagtc catggcatct tcttcttctt cttctagatg gagctatgat    4320
gttttcttaa gttttagagg cgaagatact cgaaaaacgt ttacaagtca cttatacgaa    4380
gtcttgaatg ataagggaat aaaaaccttt caagatgata aaaggctaga gtacggcgca    4440
accatcccag gtgaactctg taaagctata gaagagtctc aatttgccat tgttgttttc    4500
tcagagaatt atgcaacatc aaggtggtgt ttgaatgaac tagtgaagat catggaatgc    4560
aaaactcgat ttaagcaaac tgttataccg atattctatg atgtggatcc atcacatgtt    4620
cggaaccaaa aggagagctt tgcaaaagcc tttgaagaac atgaaacaaa gtataaggat    4680
gatgttgagg gaatacaaag atggaggatt gctttaaatg aagcggccaa tctcaaaggc    4740
tcctgtgata atcgtgacaa gtgagttaaa aacatataag ctgaatactt tgcattcaaa    4800
tgagttaaac ataatcttaa ataaatttt caattttttg gaataaattg atagttgatt    4860
```

```
atatatgttt ctatcagtta attacaaact caataacatt attacgtaga taaaattttt    4920
attagttctt caaagagttt gatttatgtg cacactcttt gtatatatca caatcttttt    4980
acttttgtag gactgatgca gactgtattc gacagattgt tgaccaaatc tcatccaaat    5040
tatgcaagat ttctttatct tatttgcaaa acattgttgg aatagatact catttagaga    5100
aaatagaatc cttactagag ataggaatca atggtgttcg gattatgggg atctgggaa     5160 tgggggagt cggtaaaaca acaatagcaa gagctatatt tgatactctt ttaggaagaa     5220
tggatagttc ctatcaattt gatggtgctt gtttccttaa ggatattaaa gaaacaaac     5280 gtggaatgca ttctttgcaa aatgcccttc tctctgaact tttaagggaa aaagctaatt    5340
acaataatga ggaggatgga aagcaccaaa tggctagtag acttcgttcg aagaaggtcc    5400
taattgtgct tgatgatata gataataaag atcattattt ggagtattta gcaggtgatc    5460
ttgattggtt tggtaatggt agtagaatta ttataacaac tagagacaag catttgatag    5520
agaagaatga tataatatat gaggtgactg cactacccga tcatgaatcc attcaattgt    5580
tcaaacaaca tgctttcgga aaagaagttc caaatgagaa ttttgagaag cttttcattag   5640 aggtagtaaa ttatgctaaa ggccttcctt tagccctcaa agtgtggggt tctttgctgc    5700
ataacctacg attaactgaa tggaaaagtg ctatagcaca catgaaaaat aactcttatt    5760
ctggaattat tgataagctc aaaataagtt atgatggatt agagcccaaa caacaagaga    5820 tgttttaga tatagcatgc ttcttgcgag gggaagaaaa agattacatc ctacaaatcc    5880
ttgagagttg tcatattgga gctgaatacg ggttacgtat tttaattgac aaatctcttg    5940
tgttcatctc tgaatataat caggttcaaa tgcatgactt aatacaggat atgggtaaat    6000
atatagtgaa ttttcaaaaa gatcccggag aacgtagcag attatggctc gccaaggaag    6060
tcgaagaagt gatgagcaac aacacagtaa gtaagctaaa taatgcaata atatttaatt    6120
tctaatttta tattctaaag acacataggg cagtcaattc cagttatttg ttcctcttgc    6180
ttcatagtct tgacggtaca tcattttagt tgtttacttt agttagtagg atatataaa     6240 gtaatattaa ttacctcatt agtaaaaaaa aacattaatt gcctaatttg tttagtagcc    6300
gctttaattt acgttcccta attcgttttt tcttatattt tttagggatg gattagtcta    6360
gtagccactt aatctgtttg atccaatgtc tttctttgga ttaacttgaa aattttatga    6420
cattatatat aataactcaa tcattcattc actttaccat tattattttt tatataaagt    6480
tacaatttat tggtactgtt tcagttacaa ttactttcca acatggaaaa cttataaact    6540
ggactccaat aaacttataa gaaaatgta ataatagaaa ataaaattat ataattaatt    6600
acaaaaaagt atttttctga agtaacatca gtatttctta aaaagaatcc aattaacatt    6660
gtatcttaaa ctttggtatt gtaaggcgtg agaaagtagt ggccttattt caatttgacg    6720
tgaagaatag aatgcctttt aacgacataa gggaagggg caagaataag tttctattca    6780
gccgggctcg aagcagaagg tagaacgtaa tatcttttgt tggttcagct catcaagcta    6840
ttacaaaaga gtccgctcat attaacaaac ggagtttata cgacatttga aattatactt    6900
tgtagactaa tgatcttctt gttaccaggg gaccatggca atggaagcaa tttgggtttc    6960
ttcttattct agtactctac gctttagcaa tcaggccgtg aaaaatatga aaaggcttag    7020
ggtatttaac atggggaggt cgtcgacaca ttatgccatc gattatctgc ccaacaactt    7080
gcgttgtttt gtttgcacta actatccttg ggagtcattt ccatctacat ttgaactcaa    7140
aatgcttgtt cacctccaac tccgacacaa ttctctgcgt catttatgga cagaaacaaa    7200
```

```
ggtacaatag cttgaattct attttgttgt catttatttt tctctctaac tatctttgtc   7260
ctttaatttg gtgataatga acaaatatta ttgttttttg ttatgaaaca ataaaagaag   7320
aagaacaata ttgcagagaa agagggagat ggaattctta ttgaattttg gggcgattta   7380
caatggggta agacccctct atttacaggg gaaaaataac ttagcctcaa aataaagctc   7440
tttaaaagat agacattcac tctaaataga attctattat aacactttg gcgtacttcc    7500 tttttttggct agaattatga tacatgtctt taaatgaaca gaagttgctt ttgtaattta   7560
tcaggactta tgttgaaact tatgaaaatt gttattgttt atgttgtcta atactaaata   7620
taaaatacaa taatatttta tcgtaatttt ttaaaaattt gtcaaataat gcaaatgaaa   7680
aattaaattt tttggtcctt taaaaatttg agaatgaaaa agtacgagtt atacttccta   7740
aaagtttgat agtgaataat atgtaaaatt taagaatga ctaatattgg actaatactt    7800
taaaacaaat aacttaatat acaaattata gcgagacatt ttcattcgtt gtactgaatg   7860
caagaaagaa aggaaaaaaa aactcattta taatatagtt tgtcttctac tattttacct   7920
tattgcttca aatttgtatt ttatcgattt tgctatatct tatgattttt ttcacggtca   7980
atattcttct tacaagaata aatttatat acctcaagtg ttttgtcaat ttgataaata    8040 attttttctta tatgatgaac ttgtaaaata atagaattgg attcttttgc taattagtta   8100
attcaacgac ttaattattt attctcaaca ttaaaggaaa taatttagtt tttattaatt   8160
caaactctta gtatttgctc attctaattt tcagtccaat aagaattcaa ttttcaaata   8220
gtaagaaaag tcatatattt tgaattttat gttttccgaa gcattgtttg tttgtttaac   8280
tctacgggag ttttctaact cacattttgt ataataaaat tttttgagta gtagttcagt   8340
acaactctaa tattaatggg ctttaaataa ggaaatatat attacgtaaa aatttaaatc   8400
attttaaagt tctttcctac caagtaaata agggaaaatt taataacaaa aatttagttg   8460
attttaaaat cctaaatatt agaaaattaa cttaaaatat aatttcgtct agtgtaaaat   8520
ttatttttaa agggtaaaaa agacgaacga cattaagagc ctttgtaatt ttaatatagt   8580
ataaatataa ataatttacc tttattcagt ttccttaacaa gtaattttcc atatataaaa   8640
aataaatttc tatattcaca caaaaataat gtgttggccc tcgtaattca aatactatca   8700
ttcatttctt gtcagggag tagtaaatac ttttaggaaa gttagcaata agtaatcaag    8760
aaatcaagaa aacagaggtc atttgatgcc cacaaataca aatgaaaaaa caaaacaaat   8820
gttacgaaac aataaaagaa caagaatagc ctcaaagtaa aactctctga tagacattta   8880
ctctaaatag aattctattt ataacaatca aaagtttct acatttatag atagctccac    8940
tagccaaata ttttattatt ggaatcagca aaataggttg tttctttttt tattctcatt   9000
ctgtctgtgt tctaaacagc atttgccgtc tctacggagg atagatctca gctggtctaa   9060
aagattgacg cgaacaccag atttcacggg gatgccaaat ttggagtatg tgaatttgta   9120
tcaatgtagt aatcttgaag aagttcacca ttccctggga tgttgcagca aagtcattgg   9180
tttatatttg aatgattgta aaagccttaa gaggtttcca tgtgttaacg tggaatctct   9240
tgaatatctg ggtctaagaa gttgcgatag tttagagaaa ttgccagaaa tctacgggag   9300
aatgaagccg gagatacaga ttcacatgca aggctctggg ataagggaac taccatcatc   9360 tattttcag tacaaaactc atgttaccaa gctattgttg tggaatatga aaaccttgt     9420 agctcttcca agcagcatat gtaggttgaa aagtttggtt agtctgagtg tgtcgggttg   9480
ctcaaaactt gaaagcttgc cagaagagat aggggattta gacaacttac gggtgtttga   9540
tgccagtgat actctaattt tacgacctcc gtcttccatc atacgcttga acaaacttat   9600
```

```
aatcttgatg tttcgaggct tcaaagatgg agtgcacttt gagttccctc ctgtggctga   9660
aggattacac tcattggaat atctgaatct cagttactgc aatctaatag atggaggact   9720
tccggaagag attggatcct tatcctcttt gaaaaagttg atctcagta gaaataattt   9780 tgagcatttg ccttcaagta tagcccaact tggtgctctt caatccttag acttaaaaga   9840
ttgccagagg cttacacagc taccagaact tcccccagaa ttaaatgaat tgcatgtaga   9900
ttgtcatatg gctctgaaat ttatccatta tttagtaaca aagagaaaga aactacatag   9960
agtgaaactt gatgatgcac acaatgatac tatgtacaat ttgtttgcat ataccatgtt  10020
tcagaatatc tcttccatga ggcatgacat ctctgcttca gattccttgt cactaacagt  10080
atttaccggt caaccgtatc ctgaaaagat cccgagttgg ttccaccatc agggttggga  10140
tagtagtgta tcagtcaatt tgcctgaaaa ttggtatata cctgataaat tcttgggatt  10200
tgctgtatgt tactctcgta gcttaattga cacaacagct cacttgattc ccgtatgtga  10260
tgacaagatg tcgcgcatga cccagaaact tgccttatca gaatgtgata cagaatcatc  10320
caactattca gaatgggata tacatttttt ctttgtacct tttgctggct tatgggatac  10380
atctaaggca aatggaaaaa caccaaatga ttatgggatt attaggctat cttttctgg   10440 agaagagaag atgtatggac ttcgtttgtt gtataaagaa ggaccagagg ttaatgcctt   10500
gttacaaatg agggaaaata gcaatgaacc aacagaacat tccactggga taaggaggac   10560
tcaatataac aacagaactt cctttatgt aagtctctac ttctattagc tacaaagtct   10620
tcttccaaaa tcaatactcc atccgttcca gtttatgtga acctattttt tgttcgtcca   10680
ttctaaaaag aatgaccccct ttctaaattt ggaaataatt ttggttaaac ttataattct   10740
accattaacg agaagctttt ataaccacac aaatattctg gggccctttt tgaattgttt   10800
aggaccataa attccaaaag tcctcatttt ttcttaaact ccgtgcccaa tcaaacaagt   10860
tcacgtaaat tggaacggag ggaatatatt ttttcttctc attcttttcc cctatttaca   10920
ggagctcatc aatgggtgat gtacatatca acaacgagtt ttaaaggatt ccaacaagta   10980
taacttttta tgctcaaatc agctccttgt attgtggaga aagctgagta cgagatgaag   11040
ttgacgtccg ttatcctttta tgatctctct gttctttgtg ttaacttgcc tacttcatca   11100
gatgaataac agaagcccgt tcctctcatt ctcaacactg tttgcacgtc tgttgttact   11160
tgttaaaatg gatcttgata aagtaataac atctctatat tacttataag tggttttaac   11220
aagttcactc ttttgctttt gcagttcaaa tgggaacaca atgtatattg agaactagaa   11280
caatgacact gcatatatat atatatgt atgtatgtaa ttctcgtctt ttggactaga   11340
ataccttgtt tcattatgaa atgaattaac atcttcgcct ttgctgacaa gtaaccaatt   11400
acagatgaat gaaatcacct gatcaacatt cattagcttt gtattctttg acgatttcgg   11460
tttcataact ctttcccctg cagttaaaat atgtagttag cccgattgca cctctagggc   11520
gcagcggagt attaaaaaaa aaaagatctt tctcatttgt ctaagtcttg gtagtcagaa   11580
ttacgagttt gtataaagtt ggctcaaaca tcacctttgt ataagaaaaa tacatacaca   11640
cacagtagaa aagaaacaga taccttcgca aatttgattg ggaggtactg atttcttctt   11700
tcagttggcg attagcctct tgtgtcatct ttggagcttc ttatgatttt tttttcttag   11760
gtaaaattca tttaataatt tgttaatcat attactgttg ggctaaacta ccccgataca   11820
ctcataacat ggtgtgatat tgttcgcttt gggccaagcc cgtatggttt tccccaaaag   11880
gcttcgcacc attaagagat ccatacacct taaatgtaga ctcacaatct tttcagctat   11940
```

-continued

```
taatgtggca ctttattcgc atacccaaca ttatgtgtac actacaggaa ttagagttgg    12000
aacagagttt taaaactagt caaagagttt tggagctaac aaaactatct tgataaatat    12060
aatacaaaca attcgtagtg ttcagaggcg aataactat gtgattactg tagaaactta     12120
taaactttaa attttggatt cgcatttgct taccgttgat tttctatctc atttatcttg    12180
gctggttgtg ccataattaa atccattgga gggacattgt aggattagct tacgtaaatg    12240
tgcttgtaaa ttgaataacg tgagctaaca ttgttgacaa attcta                   12286
```

<210> SEQ ID NO 2
<211> LENGTH: 3756
<212> TYPE: DNA
<213> ORGANISM: Nicotiana glutinosa
<220> FEATURE:
<221> NAME/KEY: CDS
<222> LOCATION: (56)..(3487)
<223> OTHER INFORMATION:

<400> SEQUENCE: 2

```
cacaattttt tcacatacag tttcttattc ttttcagaga attaacgttg agtcc atg        58
                                                             Met
                                                               1 gca tct tct tct tct tct tct aga tgg agc tat gat gtt ttc tta agt       106
Ala Ser Ser Ser Ser Ser Ser Arg Trp Ser Tyr Asp Val Phe Leu Ser
          5                  10                  15 ttt aga ggc gaa gat act cga aaa acg ttt aca agt cac tta tac gaa       154
Phe Arg Gly Glu Asp Thr Arg Lys Thr Phe Thr Ser His Leu Tyr Glu
     20                  25                  30 gtc ttg aat gat aag gga ata aaa acc ttt caa gat gat aaa agg cta       202
Val Leu Asn Asp Lys Gly Ile Lys Thr Phe Gln Asp Asp Lys Arg Leu
 35                  40                  45 gag tac ggc gca acc atc cca ggt gaa ctc tgt aaa gct ata gaa gag       250
Glu Tyr Gly Ala Thr Ile Pro Gly Glu Leu Cys Lys Ala Ile Glu Glu
50                  55                  60                  65 tct caa ttt gcc att gtt gtt ttc tca gag aat tat gca aca tca agg       298
Ser Gln Phe Ala Ile Val Val Phe Ser Glu Asn Tyr Ala Thr Ser Arg
                 70                  75                  80 tgg tgt ttg aat gaa cta gtg aag atc atg gaa tgc aaa act cga ttt       346
Trp Cys Leu Asn Glu Leu Val Lys Ile Met Glu Cys Lys Thr Arg Phe
             85                  90                  95 aag caa act gtt ata ccg ata ttc tat gat gtg gat cca tca cat gtt       394
Lys Gln Thr Val Ile Pro Ile Phe Tyr Asp Val Asp Pro Ser His Val
        100                 105                 110 cgg aac caa aag gag agc ttt gca aaa gcc ttt gaa gaa cat gaa aca       442
Arg Asn Gln Lys Glu Ser Phe Ala Lys Ala Phe Glu Glu His Glu Thr
    115                 120                 125 aag tat aag gat gat gtt gag gga ata caa aga tgg agg att gct tta       490
Lys Tyr Lys Asp Asp Val Glu Gly Ile Gln Arg Trp Arg Ile Ala Leu
130                 135                 140                 145 aat gaa gcg gcc aat ctc aaa ggc tcc tgt gat aat cgt gac aag act       538
Asn Glu Ala Ala Asn Leu Lys Gly Ser Cys Asp Asn Arg Asp Lys Thr
                150                 155                 160 gat gca gac tgt att cga cag att gtt gac caa atc tca tcc aaa tta       586
Asp Ala Asp Cys Ile Arg Gln Ile Val Asp Gln Ile Ser Ser Lys Leu
            165                 170                 175 tgc aag att tct tta tct tat ttg caa aac att gtt gga ata gat act       634
Cys Lys Ile Ser Leu Ser Tyr Leu Gln Asn Ile Val Gly Ile Asp Thr
        180                 185                 190 cat tta gag aaa ata gaa tcc tta cta gag ata gga atc aat ggt gtt       682
His Leu Glu Lys Ile Glu Ser Leu Leu Glu Ile Gly Ile Asn Gly Val
    195                 200                 205
```

-continued

| | |
|---|---|
| cgg att atg ggg atc tgg gga atg ggg gga gtc ggt aaa aca aca ata<br>Arg Ile Met Gly Ile Trp Gly Met Gly Gly Val Gly Lys Thr Thr Ile<br>210                    215                    220                    225 | 730 |
| gca aga gct ata ttt gat act ctt tta gga aga atg gat agt tcc tat<br>Ala Arg Ala Ile Phe Asp Thr Leu Leu Gly Arg Met Asp Ser Ser Tyr<br>                    230                    235                    240 | 778 |
| caa ttt gat ggt gct tgt ttc ctt aag gat att aaa gaa aac aaa cgt<br>Gln Phe Asp Gly Ala Cys Phe Leu Lys Asp Ile Lys Glu Asn Lys Arg<br>                  245                    250                    255 | 826 |
| gga atg cat tct ttg caa aat gcc ctt ctc tct gaa ctt tta agg gaa<br>Gly Met His Ser Leu Gln Asn Ala Leu Leu Ser Glu Leu Leu Arg Glu<br>260                    265                    270 | 874 |
| aaa gct aat tac aat aat gag gag gat gga aag cac caa atg gct agt<br>Lys Ala Asn Tyr Asn Asn Glu Glu Asp Gly Lys His Gln Met Ala Ser<br>       275                    280                    285 | 922 |
| aga ctt cgt tcg aag aag gtc cta att gtg ctt gat gat ata gat aat<br>Arg Leu Arg Ser Lys Lys Val Leu Ile Val Leu Asp Asp Ile Asp Asn<br>290                    295                    300                    305 | 970 |
| aaa gat cat tat ttg gag tat tta gca ggt gat ctt gat tgg ttt ggt<br>Lys Asp His Tyr Leu Glu Tyr Leu Ala Gly Asp Leu Asp Trp Phe Gly<br>                  310                    315                    320 | 1018 |
| aat ggt agt aga att att ata aca act aga gac aag cat ttg ata gag<br>Asn Gly Ser Arg Ile Ile Ile Thr Thr Arg Asp Lys His Leu Ile Glu<br>                325                    330                    335 | 1066 |
| aag aat gat ata ata tat gag gtg act gca cta ccc gat cat gaa tcc<br>Lys Asn Asp Ile Ile Tyr Glu Val Thr Ala Leu Pro Asp His Glu Ser<br>340                    345                    350 | 1114 |
| att caa ttg ttc aaa caa cat gct ttc gga aaa gaa gtt cca aat gag<br>Ile Gln Leu Phe Lys Gln His Ala Phe Gly Lys Glu Val Pro Asn Glu<br>       355                    360                    365 | 1162 |
| aat ttt gag aag ctt tca tta gag gta gta aat tat gct aaa ggc ctt<br>Asn Phe Glu Lys Leu Ser Leu Glu Val Val Asn Tyr Ala Lys Gly Leu<br>370                    375                    380                    385 | 1210 |
| cct tta gcc ctc aaa gtg tgg ggt tct ttg ctg cat aac cta cga tta<br>Pro Leu Ala Leu Lys Val Trp Gly Ser Leu Leu His Asn Leu Arg Leu<br>                  390                    395                    400 | 1258 |
| act gaa tgg aaa agt gct ata gag cac atg aaa aat aac tct tat tct<br>Thr Glu Trp Lys Ser Ala Ile Glu His Met Lys Asn Asn Ser Tyr Ser<br>                405                    410                    415 | 1306 |
| gga att att gat aag ctc aaa ata agt tat gat gga tta gag ccc aaa<br>Gly Ile Ile Asp Lys Leu Lys Ile Ser Tyr Asp Gly Leu Glu Pro Lys<br>                  420                    425                    430 | 1354 |
| caa caa gag atg ttt tta gat ata gca tgc ttc ttg cga ggg gaa gaa<br>Gln Gln Glu Met Phe Leu Asp Ile Ala Cys Phe Leu Arg Gly Glu Glu<br>435                    440                    445 | 1402 |
| aaa gat tac atc cta caa atc ctt gag agt tgt cat att gga gct gaa<br>Lys Asp Tyr Ile Leu Gln Ile Leu Glu Ser Cys His Ile Gly Ala Glu<br>450                    455                    460                    465 | 1450 |
| tac ggg tta cgt att tta att gac aaa tct ctt gtg ttc atc tct gaa<br>Tyr Gly Leu Arg Ile Leu Ile Asp Lys Ser Leu Val Phe Ile Ser Glu<br>                  470                    475                    480 | 1498 |
| tat aat cag gtt caa atg cat gac tta ata cag gat atg ggt aaa tat<br>Tyr Asn Gln Val Gln Met His Asp Leu Ile Gln Asp Met Gly Lys Tyr<br>                485                    490                    495 | 1546 |
| ata gtg aat ttt caa aaa gat ccc gga gaa cgt agc aga tta tgg ctc<br>Ile Val Asn Phe Gln Lys Asp Pro Gly Glu Arg Ser Arg Leu Trp Leu<br>                500                    505                    510 | 1594 |
| gcc aag gaa gtc gaa gaa gtg atg agc aac aac aca ggg acc atg gca<br>Ala Lys Glu Val Glu Glu Val Met Ser Asn Asn Thr Gly Thr Met Ala | 1642 |

```
          515                 520                 525
atg gaa gca att tgg gtt tct tct tat tct agt act cta cgc ttt agc    1690
Met Glu Ala Ile Trp Val Ser Ser Tyr Ser Ser Thr Leu Arg Phe Ser
530                 535                 540                 545 aat cag gcc gtg aaa aat atg aaa agg ctt agg gta ttt aac atg ggg    1738
Asn Gln Ala Val Lys Asn Met Lys Arg Leu Arg Val Phe Asn Met Gly
                550                 555                 560 agg tcg tcg aca cat tat gcc atc gat tat ctg ccc aac aac ttg cgt    1786
Arg Ser Ser Thr His Tyr Ala Ile Asp Tyr Leu Pro Asn Asn Leu Arg
            565                 570                 575 tgt ttt gtt tgc act aac tat cct tgg gag tca ttt cca tct aca ttt    1834
Cys Phe Val Cys Thr Asn Tyr Pro Trp Glu Ser Phe Pro Ser Thr Phe
        580                 585                 590 gaa ctc aaa atg ctt gtt cac ctc caa ctc cga cac aat tct ctg cgt    1882
Glu Leu Lys Met Leu Val His Leu Gln Leu Arg His Asn Ser Leu Arg
    595                 600                 605 cat tta tgg aca gaa aca aag cat ttg ccg tct cta cgg agg ata gat    1930
His Leu Trp Thr Glu Thr Lys His Leu Pro Ser Leu Arg Arg Ile Asp
610                 615                 620                 625 ctc agc tgg tct aaa aga ttg acg cga aca cca gat ttc acg ggg atg    1978
Leu Ser Trp Ser Lys Arg Leu Thr Arg Thr Pro Asp Phe Thr Gly Met
                630                 635                 640 cca aat ttg gag tat gtg aat ttg tat caa tgt agt aat ctt gaa gaa    2026
Pro Asn Leu Glu Tyr Val Asn Leu Tyr Gln Cys Ser Asn Leu Glu Glu
            645                 650                 655 gtt cac cat tcc ctg gga tgt tgc agc aaa gtc att ggt tta tat ttg    2074
Val His His Ser Leu Gly Cys Cys Ser Lys Val Ile Gly Leu Tyr Leu
        660                 665                 670 aat gat tgt aaa agc ctt aag agg ttt cca tgt gtt aac gtg gaa tct    2122
Asn Asp Cys Lys Ser Leu Lys Arg Phe Pro Cys Val Asn Val Glu Ser
    675                 680                 685 ctt gaa tat ctg ggt cta aga agt tgc gat agt tta gag aaa ttg cca    2170
Leu Glu Tyr Leu Gly Leu Arg Ser Cys Asp Ser Leu Glu Lys Leu Pro
690                 695                 700                 705 gaa atc tac ggg aga atg aag ccg gag ata cag att cac atg caa ggc    2218
Glu Ile Tyr Gly Arg Met Lys Pro Glu Ile Gln Ile His Met Gln Gly
                710                 715                 720 tct ggg ata agg gaa cta cca tca tct att ttt cag tac aaa act cat    2266
Ser Gly Ile Arg Glu Leu Pro Ser Ser Ile Phe Gln Tyr Lys Thr His
            725                 730                 735 gtt acc aag cta ttg ttg tgg aat atg aaa aac ctt gta gct ctt cca    2314
Val Thr Lys Leu Leu Leu Trp Asn Met Lys Asn Leu Val Ala Leu Pro
        740                 745                 750 agc agc ata tgt agg ttg aaa agt ttg gtt agt ctg agt gtg tcg ggt    2362
Ser Ser Ile Cys Arg Leu Lys Ser Leu Val Ser Leu Ser Val Ser Gly
    755                 760                 765 tgc tca aaa ctt gaa agc ttg cca gaa gag ata ggg gat tta gac aac    2410
Cys Ser Lys Leu Glu Ser Leu Pro Glu Glu Ile Gly Asp Leu Asp Asn
770                 775                 780                 785 tta cgg gtg ttt gat gcc agt gat act cta att tta cga cct ccg tct    2458
Leu Arg Val Phe Asp Ala Ser Asp Thr Leu Ile Leu Arg Pro Pro Ser
                790                 795                 800 tcc atc ata cgc ttg aac aaa ctt ata atc ttg atg ttt cga ggc ttc    2506
Ser Ile Ile Arg Leu Asn Lys Leu Ile Ile Leu Met Phe Arg Gly Phe
            805                 810                 815 aaa gat gga gtg cac ttt gag ttc cct cct gtg gct gaa gga tta cac    2554
Lys Asp Gly Val His Phe Glu Phe Pro Pro Val Ala Glu Gly Leu His
        820                 825                 830 tca ttg gaa tat ctg aat ctc agt tac tgc aat cta ata gat gga gga    2602
```

```
                                                                -continued

Ser Leu Glu Tyr Leu Asn Leu Ser Tyr Cys Asn Leu Ile Asp Gly Gly
    835                 840                 845 ctt ccg gaa gag att gga tcc tta tcc tct ttg aaa aag ttg gat ctc      2650
Leu Pro Glu Glu Ile Gly Ser Leu Ser Ser Leu Lys Lys Leu Asp Leu
850                 855                 860                 865 agt aga aat aat ttt gag cat ttg cct tca agt ata gcc caa ctt ggt      2698
Ser Arg Asn Asn Phe Glu His Leu Pro Ser Ser Ile Ala Gln Leu Gly
                870                 875                 880 gct ctt caa tcc tta gac tta aaa gat tgc cag agg ctt aca cag cta      2746
Ala Leu Gln Ser Leu Asp Leu Lys Asp Cys Gln Arg Leu Thr Gln Leu
            885                 890                 895 cca gaa ctt ccc cca gaa tta aat gaa ttg cat gta gat tgt cat atg      2794
Pro Glu Leu Pro Pro Glu Leu Asn Glu Leu His Val Asp Cys His Met
        900                 905                 910 gct ctg aaa ttt atc cat tat tta gta aca aag aga aag aaa cta cat      2842
Ala Leu Lys Phe Ile His Tyr Leu Val Thr Lys Arg Lys Lys Leu His
    915                 920                 925 aga gtg aaa ctt gat gat gca cac aat gat act atg tac aat ttg ttt      2890
Arg Val Lys Leu Asp Asp Ala His Asn Asp Thr Met Tyr Asn Leu Phe
930                 935                 940                 945 gca tat acc atg ttt cag aat atc tct tcc atg agg cat gac atc tct      2938
Ala Tyr Thr Met Phe Gln Asn Ile Ser Ser Met Arg His Asp Ile Ser
                950                 955                 960 gct tca gat tcc ttg tca cta aca gta ttt acc ggt caa ccg tat cct      2986
Ala Ser Asp Ser Leu Ser Leu Thr Val Phe Thr Gly Gln Pro Tyr Pro
            965                 970                 975 gaa aag atc ccg agt tgg ttc cac cat cag ggt tgg gat agt agt gta      3034
Glu Lys Ile Pro Ser Trp Phe His His Gln Gly Trp Asp Ser Ser Val
        980                 985                 990 tca gtc aat ttg cct gaa aat tgg tat ata cct gat aaa ttc ttg gga      3082
Ser Val Asn Leu Pro Glu Asn Trp Tyr Ile Pro Asp Lys Phe Leu Gly
    995                 1000                1005 ttt gct gta tgt tac tct cgt agc tta att gac aca aca gct cac           3127
Phe Ala Val Cys Tyr Ser Arg Ser Leu Ile Asp Thr Thr Ala His
1010                1015                1020 ttg att ccc gta tgt gat gac aag atg tcg cgc atg acc cag aaa           3172
Leu Ile Pro Val Cys Asp Asp Lys Met Ser Arg Met Thr Gln Lys
1025                1030                1035 ctt gcc tta tca gaa tgt gat aca gaa tca tcc aac tat tca gaa           3217
Leu Ala Leu Ser Glu Cys Asp Thr Glu Ser Ser Asn Tyr Ser Glu
1040                1045                1050 tgg gat ata cat ttt ttc ttt gta cct ttt gct ggc tta tgg gat           3262
Trp Asp Ile His Phe Phe Phe Val Pro Phe Ala Gly Leu Trp Asp
1055                1060                1065 aca tct aag gca aat gga aaa aca cca aat gat tat ggg att att           3307
Thr Ser Lys Ala Asn Gly Lys Thr Pro Asn Asp Tyr Gly Ile Ile
1070                1075                1080 agg cta tct ttt tct gga gaa gag aag atg tat gga ctt cgt ttg           3352
Arg Leu Ser Phe Ser Gly Glu Glu Lys Met Tyr Gly Leu Arg Leu
1085                1090                1095 ttg tat aaa gaa gga cca gag gtt aat gcc ttg tta caa atg agg           3397
Leu Tyr Lys Glu Gly Pro Glu Val Asn Ala Leu Leu Gln Met Arg
1100                1105                1110 gaa aat agc aat gaa cca aca gaa cat tcc act ggg ata agg agg           3442
Glu Asn Ser Asn Glu Pro Thr Glu His Ser Thr Gly Ile Arg Arg
1115                1120                1125 act caa tat aac aac aga act tcc ttt tat gag ctc atc aat ggg           3487
Thr Gln Tyr Asn Asn Arg Thr Ser Phe Tyr Glu Leu Ile Asn Gly
1130                1135                1140
```

-continued

```
tgatgtacat atcaacaacg agttttaaag gattccaaca agtataactt tttatgctca    3547
aatcagctcc ttgtattgtg agaaagctg agtacgagat gaagttgacg tccgttatcc     3607
tttatgatct ctctgttctt tgtgttaact tgcctacttc atcagatgaa taacagaagc    3667
ccgttcctct cattctcaac actgtttgca cgtctgttgt tacttgttaa aatggatctt    3727
gataaagtaa taacatctct atattactt                                      3756
```

<210> SEQ ID NO 3
<211> LENGTH: 1144
<212> TYPE: PRT
<213> ORGANISM: Nicotiana glutinosa

<400> SEQUENCE: 3

```
Met Ala Ser Ser Ser Ser Ser Arg Trp Ser Tyr Asp Val Phe Leu
1               5                   10                  15

Ser Phe Arg Gly Glu Asp Thr Arg Lys Thr Phe Thr Ser His Leu Tyr
            20                  25                  30

Glu Val Leu Asn Asp Lys Gly Ile Lys Thr Phe Gln Asp Asp Lys Arg
        35                  40                  45

Leu Glu Tyr Gly Ala Thr Ile Pro Gly Glu Leu Cys Lys Ala Ile Glu
    50                  55                  60

Glu Ser Gln Phe Ala Ile Val Val Phe Ser Glu Asn Tyr Ala Thr Ser
65                  70                  75                  80

Arg Trp Cys Leu Asn Glu Leu Val Lys Ile Met Glu Cys Lys Thr Arg
                85                  90                  95

Phe Lys Gln Thr Val Ile Pro Ile Phe Tyr Asp Val Asp Pro Ser His
            100                 105                 110

Val Arg Asn Gln Lys Glu Ser Phe Ala Lys Ala Phe Glu Glu His Glu
        115                 120                 125

Thr Lys Tyr Lys Asp Asp Val Glu Gly Ile Gln Arg Trp Arg Ile Ala
    130                 135                 140

Leu Asn Glu Ala Ala Asn Leu Lys Gly Ser Cys Asp Asn Arg Asp Lys
145                 150                 155                 160

Thr Asp Ala Asp Cys Ile Arg Gln Ile Val Asp Gln Ile Ser Ser Lys
                165                 170                 175

Leu Cys Lys Ile Ser Leu Ser Tyr Leu Gln Asn Ile Val Gly Ile Asp
            180                 185                 190

Thr His Leu Glu Lys Ile Glu Ser Leu Leu Glu Ile Gly Ile Asn Gly
        195                 200                 205

Val Arg Ile Met Gly Ile Trp Gly Met Gly Gly Val Gly Lys Thr Thr
    210                 215                 220

Ile Ala Arg Ala Ile Phe Asp Thr Leu Leu Gly Arg Met Asp Ser Ser
225                 230                 235                 240

Tyr Gln Phe Asp Gly Ala Cys Phe Leu Lys Asp Ile Lys Glu Asn Lys
                245                 250                 255

Arg Gly Met His Ser Leu Gln Asn Ala Leu Leu Ser Glu Leu Leu Arg
            260                 265                 270

Glu Lys Ala Asn Tyr Asn Asn Glu Glu Asp Gly Lys His Gln Met Ala
        275                 280                 285

Ser Arg Leu Arg Ser Lys Lys Val Leu Ile Val Leu Asp Asp Ile Asp
    290                 295                 300

Asn Lys Asp His Tyr Leu Glu Tyr Leu Ala Gly Asp Leu Asp Trp Phe
305                 310                 315                 320

Gly Asn Gly Ser Arg Ile Ile Ile Thr Thr Arg Asp Lys His Leu Ile
```

-continued

```
                325                 330                 335
Glu Lys Asn Asp Ile Ile Tyr Glu Val Thr Ala Leu Pro Asp His Glu
                340                 345                 350
Ser Ile Gln Leu Phe Lys Gln His Ala Phe Gly Lys Glu Val Pro Asn
                355                 360                 365
Glu Asn Phe Glu Lys Leu Ser Leu Glu Val Val Asn Tyr Ala Lys Gly
                370                 375                 380
Leu Pro Leu Ala Leu Lys Val Trp Gly Ser Leu His Asn Leu Arg
385                 390                 395                 400
Leu Thr Glu Trp Lys Ser Ala Ile Glu His Met Lys Asn Asn Ser Tyr
                405                 410                 415
Ser Gly Ile Ile Asp Lys Leu Lys Ile Ser Tyr Asp Gly Leu Glu Pro
                420                 425                 430
Lys Gln Gln Glu Met Phe Leu Asp Ile Ala Cys Phe Leu Arg Gly Glu
                435                 440                 445
Glu Lys Asp Tyr Ile Leu Gln Ile Leu Glu Ser Cys His Ile Gly Ala
                450                 455                 460
Glu Tyr Gly Leu Arg Ile Leu Ile Asp Lys Ser Leu Val Phe Ile Ser
465                 470                 475                 480
Glu Tyr Asn Gln Val Gln Met His Asp Leu Ile Gln Asp Met Gly Lys
                485                 490                 495
Tyr Ile Val Asn Phe Gln Lys Asp Pro Gly Glu Arg Ser Arg Leu Trp
                500                 505                 510
Leu Ala Lys Glu Val Glu Glu Val Met Ser Asn Asn Thr Gly Thr Met
                515                 520                 525
Ala Met Glu Ala Ile Trp Val Ser Ser Tyr Ser Ser Thr Leu Arg Phe
                530                 535                 540
Ser Asn Gln Ala Val Lys Asn Met Lys Arg Leu Arg Val Phe Asn Met
545                 550                 555                 560
Gly Arg Ser Ser Thr His Tyr Ala Ile Asp Tyr Leu Pro Asn Asn Leu
                565                 570                 575
Arg Cys Phe Val Cys Thr Asn Tyr Pro Trp Glu Ser Phe Pro Ser Thr
                580                 585                 590
Phe Glu Leu Lys Met Leu Val His Leu Gln Leu Arg His Asn Ser Leu
                595                 600                 605
Arg His Leu Trp Thr Glu Thr Lys His Leu Pro Ser Leu Arg Arg Ile
                610                 615                 620
Asp Leu Ser Trp Ser Lys Arg Leu Thr Arg Thr Pro Asp Phe Thr Gly
625                 630                 635                 640
Met Pro Asn Leu Glu Tyr Val Asn Leu Tyr Gln Cys Ser Asn Leu Glu
                645                 650                 655
Glu Val His His Ser Leu Gly Cys Cys Ser Lys Val Ile Gly Leu Tyr
                660                 665                 670
Leu Asn Asp Cys Lys Ser Leu Lys Arg Phe Pro Cys Val Asn Val Glu
                675                 680                 685
Ser Leu Glu Tyr Leu Gly Leu Arg Ser Cys Asp Ser Leu Glu Lys Leu
                690                 695                 700
Pro Glu Ile Tyr Gly Arg Met Lys Pro Glu Ile Gln Ile His Met Gln
705                 710                 715                 720
Gly Ser Gly Ile Arg Glu Leu Pro Ser Ser Ile Phe Gln Tyr Lys Thr
                725                 730                 735
His Val Thr Lys Leu Leu Leu Trp Asn Met Lys Asn Leu Val Ala Leu
                740                 745                 750
```

```
Pro Ser Ser Ile Cys Arg Leu Lys Ser Leu Val Ser Leu Ser Val Ser
        755                 760                 765
Gly Cys Ser Lys Leu Glu Ser Leu Pro Glu Glu Ile Gly Asp Leu Asp
        770                 775                 780
Asn Leu Arg Val Phe Asp Ala Ser Asp Thr Leu Ile Leu Arg Pro Pro
785                 790                 795                 800
Ser Ser Ile Ile Arg Leu Asn Lys Leu Ile Ile Leu Met Phe Arg Gly
                805                 810                 815
Phe Lys Asp Gly Val His Phe Glu Phe Pro Pro Val Ala Glu Gly Leu
                820                 825                 830
His Ser Leu Glu Tyr Leu Asn Leu Ser Tyr Cys Asn Leu Ile Asp Gly
                835                 840                 845
Gly Leu Pro Glu Glu Ile Gly Ser Leu Ser Ser Leu Lys Lys Leu Asp
        850                 855                 860
Leu Ser Arg Asn Asn Phe Glu His Leu Pro Ser Ser Ile Ala Gln Leu
865                 870                 875                 880
Gly Ala Leu Gln Ser Leu Asp Leu Lys Asp Cys Gln Arg Leu Thr Gln
                885                 890                 895
Leu Pro Glu Leu Pro Pro Glu Leu Asn Glu Leu His Val Asp Cys His
        900                 905                 910
Met Ala Leu Lys Phe Ile His Tyr Leu Val Thr Lys Arg Lys Lys Leu
        915                 920                 925
His Arg Val Lys Leu Asp Asp Ala His Asn Asp Thr Met Tyr Asn Leu
        930                 935                 940
Phe Ala Tyr Thr Met Phe Gln Asn Ile Ser Ser Met Arg His Asp Ile
945                 950                 955                 960
Ser Ala Ser Asp Ser Leu Ser Leu Thr Val Phe Thr Gly Gln Pro Tyr
                965                 970                 975
Pro Glu Lys Ile Pro Ser Trp Phe His His Gln Gly Trp Asp Ser Ser
                980                 985                 990
Val Ser Val Asn Leu Pro Glu Asn Trp Tyr Ile Pro Asp Lys Phe Leu
                995                 1000                1005
Gly Phe Ala Val Cys Tyr Ser Arg Ser Leu Ile Asp Thr Thr Ala
        1010                1015                1020
His Leu Ile Pro Val Cys Asp Asp Lys Met Ser Arg Met Thr Gln
        1025                1030                1035
Lys Leu Ala Leu Ser Glu Cys Asp Thr Glu Ser Ser Asn Tyr Ser
        1040                1045                1050
Glu Trp Asp Ile His Phe Phe Val Pro Phe Ala Gly Leu Trp
        1055                1060                1065
Asp Thr Ser Lys Ala Asn Gly Lys Thr Pro Asn Asp Tyr Gly Ile
        1070                1075                1080
Ile Arg Leu Ser Phe Ser Gly Glu Glu Lys Met Tyr Gly Leu Arg
        1085                1090                1095
Leu Leu Tyr Lys Glu Gly Pro Glu Val Asn Ala Leu Leu Gln Met
        1100                1105                1110
Arg Glu Asn Ser Asn Glu Pro Thr Glu His Ser Thr Gly Ile Arg
        1115                1120                1125
Arg Thr Gln Tyr Asn Asn Arg Thr Ser Phe Tyr Glu Leu Ile Asn
        1130                1135                1140
Gly
```

-continued

```
<210> SEQ ID NO 4
<211> LENGTH: 3826
<212> TYPE: DNA
<213> ORGANISM: Nicotiana glutinosa
<220> FEATURE:
<221> NAME/KEY: CDS
<222> LOCATION: (56)..(2011)
<223> OTHER INFORMATION:

<400> SEQUENCE: 4
```

| | | |
|---|---|---|
| cacaatttttt tcacatacag tttcttattc ttttcagaga attaacgttg agtcc atg<br>                                                                    Met<br>                                                                     1 | | 58 |
| gca tct tct tct tct tct aga tgg agc tat gat gtt ttc tta agt<br>Ala Ser Ser Ser Ser Ser Arg Trp Ser Tyr Asp Val Phe Leu Ser<br>         5                   10                  15 | | 106 |
| ttt aga ggc gaa gat act cga aaa acg ttt aca agt cac tta tac gaa<br>Phe Arg Gly Glu Asp Thr Arg Lys Thr Phe Thr Ser His Leu Tyr Glu<br>         20                  25                  30 | | 154 |
| gtc ttg aat gat aag gga ata aaa acc ttt caa gat gat aaa agg cta<br>Val Leu Asn Asp Lys Gly Ile Lys Thr Phe Gln Asp Asp Lys Arg Leu<br>     35                  40                  45 | | 202 |
| gag tac ggc gca acc atc cca ggt gaa ctc tgt aaa gct ata gaa gag<br>Glu Tyr Gly Ala Thr Ile Pro Gly Glu Leu Cys Lys Ala Ile Glu Glu<br>50                  55                  60                  65 | | 250 |
| tct caa ttt gcc att gtt gtt ttc tca gag aat tat gca aca tca agg<br>Ser Gln Phe Ala Ile Val Val Phe Ser Glu Asn Tyr Ala Thr Ser Arg<br>                 70                  75                  80 | | 298 |
| tgg tgt ttg aat gaa cta gtg aag atc atg gaa tgc aaa act cga ttt<br>Trp Cys Leu Asn Glu Leu Val Lys Ile Met Glu Cys Lys Thr Arg Phe<br>             85                  90                  95 | | 346 |
| aag caa act gtt ata ccg ata ttc tat gat gtg gat cca tca cat gtt<br>Lys Gln Thr Val Ile Pro Ile Phe Tyr Asp Val Asp Pro Ser His Val<br>         100                 105                 110 | | 394 |
| cgg aac caa aag gag agc ttt gca aaa gcc ttt gaa gaa cat gaa aca<br>Arg Asn Gln Lys Glu Ser Phe Ala Lys Ala Phe Glu Glu His Glu Thr<br>     115                 120                 125 | | 442 |
| aag tat aag gat gat gtt gag gga ata caa aga tgg agg att gct tta<br>Lys Tyr Lys Asp Asp Val Glu Gly Ile Gln Arg Trp Arg Ile Ala Leu<br>130                 135                 140                 145 | | 490 |
| aat gaa gcg gcc aat ctc aaa ggc tca tgt gat aat cgt gac aag act<br>Asn Glu Ala Ala Asn Leu Lys Gly Ser Cys Asp Asn Arg Asp Lys Thr<br>                 150                 155                 160 | | 538 |
| gat gca gac tgt att cga cag att gtt gac caa atc tca tcc aaa tta<br>Asp Ala Asp Cys Ile Arg Gln Ile Val Asp Gln Ile Ser Ser Lys Leu<br>             165                 170                 175 | | 586 |
| tgc aag att tct tta tct tat ttg caa aac att gtt gga ata gat act<br>Cys Lys Ile Ser Leu Ser Tyr Leu Gln Asn Ile Val Gly Ile Asp Thr<br>         180                 185                 190 | | 634 |
| cat tta gag aaa ata gaa tcc tta cta gag ata gga atc aat ggt gtt<br>His Leu Glu Lys Ile Glu Ser Leu Leu Glu Ile Gly Ile Asn Gly Val<br>     195                 200                 205 | | 682 |
| cgg att atg ggg atc tgg gga atg ggg gga gtc ggt aaa aca aca ata<br>Arg Ile Met Gly Ile Trp Gly Met Gly Gly Val Gly Lys Thr Thr Ile<br>210                 215                 220                 225 | | 730 |
| gca aga gct ata ttt gat act ctt tta gga aga atg gat agt tcc tat<br>Ala Arg Ala Ile Phe Asp Thr Leu Leu Gly Arg Met Asp Ser Ser Tyr<br>                 230                 235                 240 | | 778 |
| caa ttt gat ggt gct tgt ttc ctt aag gat att aaa gaa aac aaa cgt<br>Gln Phe Asp Gly Ala Cys Phe Leu Lys Asp Ile Lys Glu Asn Lys Arg<br>             245                 250                 255 | | 826 |

```
gga atg cat tct ttg caa aat gcc ctt ctc tct gaa ctt tta agg gaa   874
Gly Met His Ser Leu Gln Asn Ala Leu Leu Ser Glu Leu Leu Arg Glu
        260                 265                 270 aaa gct aat tac aat aat gag gag gat gga aag cac caa atg gct agt   922
Lys Ala Asn Tyr Asn Asn Glu Glu Asp Gly Lys His Gln Met Ala Ser
    275                 280                 285 aga ctt cgt tcg aag aag gtc cta att gtg ctt gat gat ata gat aat   970
Arg Leu Arg Ser Lys Lys Val Leu Ile Val Leu Asp Asp Ile Asp Asn
290                 295                 300                 305 aaa gat cat tat ttg gag tat tta gca ggt gat ctt gat tgg ttt ggt  1018
Lys Asp His Tyr Leu Glu Tyr Leu Ala Gly Asp Leu Asp Trp Phe Gly
            310                 315                 320 aat ggt agt aga att att ata aca act aga gac aag cat ttg ata gag  1066
Asn Gly Ser Arg Ile Ile Ile Thr Thr Arg Asp Lys His Leu Ile Glu
        325                 330                 335 aag aat gat ata ata tat gag gtg act gca cta ccc gat cat gaa tcc  1114
Lys Asn Asp Ile Ile Tyr Glu Val Thr Ala Leu Pro Asp His Glu Ser
    340                 345                 350 att caa ttg ttc aaa caa cat gct ttc gga aaa gaa gtt cca aat gag  1162
Ile Gln Leu Phe Lys Gln His Ala Phe Gly Lys Glu Val Pro Asn Glu
355                 360                 365 aat ttt gag aag ctt tca tta gag gta gta aat tat gct aaa ggc ctt  1210
Asn Phe Glu Lys Leu Ser Leu Glu Val Val Asn Tyr Ala Lys Gly Leu
370                 375                 380                 385 cct tta gcc ctc aaa gtg tgg ggt tct ttg ctg cat aac cta cga tta  1258
Pro Leu Ala Leu Lys Val Trp Gly Ser Leu Leu His Asn Leu Arg Leu
            390                 395                 400 act gaa tgg aaa agt gct ata gag cac atg aaa aat aac tct tat tct  1306
Thr Glu Trp Lys Ser Ala Ile Glu His Met Lys Asn Asn Ser Tyr Ser
        405                 410                 415 gga att att gat aag ctc aaa ata agt tat gat gga tta gag ccc aaa  1354
Gly Ile Ile Asp Lys Leu Lys Ile Ser Tyr Asp Gly Leu Glu Pro Lys
    420                 425                 430 caa caa gag atg ttt tta gat ata gca tgc ttc ttg cga ggg gaa gaa  1402
Gln Gln Glu Met Phe Leu Asp Ile Ala Cys Phe Leu Arg Gly Glu Glu
435                 440                 445 aaa gat tac atc cta caa atc ctt gag agt tgt cat att gga gct gaa  1450
Lys Asp Tyr Ile Leu Gln Ile Leu Glu Ser Cys His Ile Gly Ala Glu
450                 455                 460                 465 tac ggg tta cgt att tta att gac aaa tct ctt gtg ttc atc tct gaa  1498
Tyr Gly Leu Arg Ile Leu Ile Asp Lys Ser Leu Val Phe Ile Ser Glu
            470                 475                 480 tat aat cag gtt caa atg cat gac tta ata cag gat atg ggt aaa tat  1546
Tyr Asn Gln Val Gln Met His Asp Leu Ile Gln Asp Met Gly Lys Tyr
        485                 490                 495 ata gtg aat ttt caa aaa gat ccc gga gaa cgt agc aga tta tgg ctc  1594
Ile Val Asn Phe Gln Lys Asp Pro Gly Glu Arg Ser Arg Leu Trp Leu
    500                 505                 510 gcc aag gaa gtc gaa gaa gtg atg agc aac aac aca ggg acc atg gca  1642
Ala Lys Glu Val Glu Glu Val Met Ser Asn Asn Thr Gly Thr Met Ala
515                 520                 525 atg gaa gca att tgg gtt tct tct tat tct agt act cta cgc ttt agc  1690
Met Glu Ala Ile Trp Val Ser Ser Tyr Ser Ser Thr Leu Arg Phe Ser
530                 535                 540                 545 aat cag gcc gtg aaa aat atg aaa agg ctt agg gta ttt aac atg ggg  1738
Asn Gln Ala Val Lys Asn Met Lys Arg Leu Arg Val Phe Asn Met Gly
            550                 555                 560 agg tcg tcg aca cat tat gcc atc gat tat ctg ccc aac aac ttg cgt  1786
Arg Ser Ser Thr His Tyr Ala Ile Asp Tyr Leu Pro Asn Asn Leu Arg
        565                 570                 575
```

-continued

| | | | | | | | | | | | | | | | |
|---|---|---|---|---|---|---|---|---|---|---|---|---|---|---|---|
| tgt | ttt | gtt | tgc | act | aac | tat | cct | tgg | gag | tca | ttt | cca | tct | aca | ttt | 1834 |
| Cys | Phe | Val | Cys | Thr | Asn | Tyr | Pro | Trp | Glu | Ser | Phe | Pro | Ser | Thr | Phe | |
| | | | 580 | | | | 585 | | | | 590 | | | | | |

| | | | | | | | | | | | | | | | |
|---|---|---|---|---|---|---|---|---|---|---|---|---|---|---|---|
| gaa | ctc | aaa | atg | ctt | gtt | cac | ctc | caa | ctc | cga | cac | aat | tct | ctg | cgt | 1882 |
| Glu | Leu | Lys | Met | Leu | Val | His | Leu | Gln | Leu | Arg | His | Asn | Ser | Leu | Arg | |
| | 595 | | | | 600 | | | | 605 | | | | | | | |

| | | | | | | | | | | | | | | | |
|---|---|---|---|---|---|---|---|---|---|---|---|---|---|---|---|
| cat | tta | tgg | aca | gaa | aca | aag | aag | aag | aac | aat | att | gca | gag | aaa | gag | 1930 |
| His | Leu | Trp | Thr | Glu | Thr | Lys | Lys | Lys | Asn | Asn | Ile | Ala | Glu | Lys | Glu | |
| 610 | | | | 615 | | | | 620 | | | | 625 | | | | |

| | | | | | | | | | | | | | | | |
|---|---|---|---|---|---|---|---|---|---|---|---|---|---|---|---|
| gga | gat | gga | att | ctt | att | gaa | ttt | tgg | ggc | gat | tta | caa | tgg | gca | ttt | 1978 |
| Gly | Asp | Gly | Ile | Leu | Ile | Glu | Phe | Trp | Gly | Asp | Leu | Gln | Trp | Ala | Phe | |
| | | | 630 | | | | 635 | | | | 640 | | | | | |

| | | | | | | | | | | |
|---|---|---|---|---|---|---|---|---|---|---|
| gcc | gtc | tct | acg | gag | gat | aga | tct | cag | ctg | gtc | taaaagattg acgcgaacac | 2031 |
| Ala | Val | Ser | Thr | Glu | Asp | Arg | Ser | Gln | Leu | Val | |
| | | | 645 | | | | 650 | | | | |

| | | |
|---|---|---|
| cagatttcac ggggatgcca aatttggagt atgtgaattt gtatcaatgt agtaatcttg | 2091 |
| aagaagttca ccattccctg ggatgttgca gcaaagtcat tggtttatat ttgaatgatt | 2151 |
| gtaaaagcct taagaggttt ccatgtgtta acgtggaatc tcttgaatat ctgggtctaa | 2211 |
| gaagttgcga tagtttagag aaattgccag aaatctacgg gagaatgaag ccggagatac | 2271 |
| agattcacat gcaaggctct gggataaggg aactaccatc atctattttt cagtacaaaa | 2331 |
| ctcatgttac caagctattg ttgtggaata tgaaaaacct tgtagctctt ccaagcagca | 2391 |
| tatgtaggtt gaaaagtttg gttagtctga gtgtgtcggg ttgctcaaaa cttgaaagct | 2451 |
| tgccagaaga gatagggggat ttagacaact tacgggtgtt tgatgccagt gatactctaa | 2511 |
| ttttacgacc tccgtcttcc atcatacgct gaacaaact tataatcttg atgtttcgag | 2571 |
| gcttcaaaga tggagtgcac tttgagttcc ctcctgtggc tgaaggatta cactcattgg | 2631 |
| aatatctgaa tctcagttac tgcaatctaa tagatggagg acttccggaa gagattggat | 2691 |
| ccttatcctc tttgaaaaag ttggatctca gtagaaataa ttttgagcat ttgccttcaa | 2751 |
| gtatagccca acttggtgct cttcaatcct tagacttaaa agattgccag aggcttacac | 2811 |
| agctaccaga acttccccca gaattaaatg aattgcatgt agattgtcat atggctctga | 2871 |
| aatttatcca tgatttagta acaaagagaa agaaactaca tagagtgaaa cttgatgatg | 2931 |
| cacacaatga tactatgtac aatttgtttg catataccat gtttcagaat atctcttcca | 2991 |
| tgaggcatga catctctgct tcagattcct tgtcactaac agtatttacc ggtcaaccgt | 3051 |
| atcctgaaaa gatcccgagt tggttccacc atcagggttg ggatagtagt gtatcagtca | 3111 |
| atttgcctga aaattggtat atacctgata aattcttggg atttgctgta tgttactctc | 3171 |
| gtagcttaat tgacacaaca gctcacttga ttcccgtatg tgatgacaag atgtcgcgca | 3231 |
| tgacccagaa acttgcctta tcagaatgtg atacagaatc atccaactat tcagaatggg | 3291 |
| atatacattt tttctttgta ccttttgctg gcttatggga tacatctaag gcaaatggaa | 3351 |
| aaacaccaaa tgattatggg attattaggc tatctttttc tggagaagag aagatgtatg | 3411 |
| gacttcgttt gttgtataaa gaaggaccag aggttaatgc cttgttacaa atgagggaaa | 3471 |
| atagcaatga accaacagaa cattccactg ggataaggag gactcaatat aacaacagaa | 3531 |
| cttcctttta tgagctcatc aatgggtgat gtacatatca acaacgagtt ttaaaggatt | 3591 |
| ccaacaagta taacttttta tgctcaaatc agctccttgt attgtggaga aagctgagta | 3651 |
| cgagatgaag ttgacgtccg ttatcctta tgatctctct gttctttgtg ttaacttgcc | 3711 |
| tacttcatca gatgaataac agaagcccgt tcctctcatt ctcaacactg tttgcacgtc | 3771 | tgttgttact tgttaaaatg gatcttgata aagtaataac atctctatat tactt    3826

<210> SEQ ID NO 5
<211> LENGTH: 652
<212> TYPE: PRT
<213> ORGANISM: Nicotiana glutinosa

<400> SEQUENCE: 5

```
Met Ala Ser Ser Ser Ser Ser Arg Trp Ser Tyr Asp Val Phe Leu
1               5                   10                  15

Ser Phe Arg Gly Glu Asp Thr Arg Lys Thr Phe Thr Ser His Leu Tyr
            20                  25                  30

Glu Val Leu Asn Asp Lys Gly Ile Lys Thr Phe Gln Asp Asp Lys Arg
        35                  40                  45

Leu Glu Tyr Gly Ala Thr Ile Pro Gly Glu Leu Cys Lys Ala Ile Glu
    50                  55                  60

Glu Ser Gln Phe Ala Ile Val Val Phe Ser Glu Asn Tyr Ala Thr Ser
65                  70                  75                  80

Arg Trp Cys Leu Asn Glu Leu Val Lys Ile Met Glu Cys Lys Thr Arg
                85                  90                  95

Phe Lys Gln Thr Val Ile Pro Ile Phe Tyr Asp Val Asp Pro Ser His
            100                 105                 110

Val Arg Asn Gln Lys Glu Ser Phe Ala Lys Ala Phe Glu Glu His Glu
        115                 120                 125

Thr Lys Tyr Lys Asp Asp Val Glu Gly Ile Gln Arg Trp Arg Ile Ala
    130                 135                 140

Leu Asn Glu Ala Ala Asn Leu Lys Gly Ser Cys Asp Asn Arg Asp Lys
145                 150                 155                 160

Thr Asp Ala Asp Cys Ile Arg Gln Ile Val Asp Gln Ile Ser Ser Lys
                165                 170                 175

Leu Cys Lys Ile Ser Leu Ser Tyr Leu Gln Asn Ile Val Gly Ile Asp
            180                 185                 190

Thr His Leu Glu Lys Ile Glu Ser Leu Leu Glu Ile Gly Ile Asn Gly
        195                 200                 205

Val Arg Ile Met Gly Ile Trp Gly Met Gly Gly Val Gly Lys Thr Thr
    210                 215                 220

Ile Ala Arg Ala Ile Phe Asp Thr Leu Leu Gly Arg Met Asp Ser Ser
225                 230                 235                 240

Tyr Gln Phe Asp Gly Ala Cys Phe Leu Lys Asp Ile Lys Glu Asn Lys
                245                 250                 255

Arg Gly Met His Ser Leu Gln Asn Ala Leu Leu Ser Glu Leu Leu Arg
            260                 265                 270

Glu Lys Ala Asn Tyr Asn Asn Glu Glu Asp Gly Lys His Gln Met Ala
        275                 280                 285

Ser Arg Leu Arg Ser Lys Lys Val Leu Ile Val Leu Asp Asp Ile Asp
    290                 295                 300

Asn Lys Asp His Tyr Leu Glu Tyr Leu Ala Gly Asp Leu Asp Trp Phe
305                 310                 315                 320

Gly Asn Gly Ser Arg Ile Ile Ile Thr Thr Arg Asp Lys His Leu Ile
                325                 330                 335

Glu Lys Asn Asp Ile Ile Tyr Glu Val Thr Ala Leu Pro Asp His Glu
            340                 345                 350

Ser Ile Gln Leu Phe Lys Gln His Ala Phe Gly Lys Glu Val Pro Asn
        355                 360                 365
```

-continued

```
Glu Asn Phe Glu Lys Leu Ser Leu Glu Val Val Asn Tyr Ala Lys Gly
        370                 375                 380

Leu Pro Leu Ala Leu Lys Val Trp Gly Ser Leu His Asn Leu Arg
385                 390                 395                 400

Leu Thr Glu Trp Lys Ser Ala Ile Glu His Met Lys Asn Asn Ser Tyr
                405                 410                 415

Ser Gly Ile Ile Asp Lys Leu Lys Ile Ser Tyr Asp Gly Leu Glu Pro
                420                 425                 430

Lys Gln Gln Glu Met Phe Leu Asp Ile Ala Cys Phe Leu Arg Gly Glu
                435                 440                 445

Glu Lys Asp Tyr Ile Leu Gln Ile Leu Glu Ser Cys His Ile Gly Ala
                450                 455                 460

Glu Tyr Gly Leu Arg Ile Leu Ile Asp Lys Ser Leu Val Phe Ile Ser
465                 470                 475                 480

Glu Tyr Asn Gln Val Gln Met His Asp Leu Ile Gln Asp Met Gly Lys
                485                 490                 495

Tyr Ile Val Asn Phe Gln Lys Asp Pro Gly Glu Arg Ser Arg Leu Trp
                500                 505                 510

Leu Ala Lys Glu Val Glu Val Met Ser Asn Asn Thr Gly Thr Met
                515                 520                 525

Ala Met Glu Ala Ile Trp Val Ser Ser Tyr Ser Thr Leu Arg Phe
                530                 535                 540

Ser Asn Gln Ala Val Lys Asn Met Lys Arg Leu Arg Val Phe Asn Met
545                 550                 555                 560

Gly Arg Ser Ser Thr His Tyr Ala Ile Asp Tyr Leu Pro Asn Asn Leu
                565                 570                 575

Arg Cys Phe Val Cys Thr Asn Tyr Pro Trp Glu Ser Phe Pro Ser Thr
                580                 585                 590

Phe Glu Leu Lys Met Leu Val His Leu Gln Leu Arg His Asn Ser Leu
                595                 600                 605

Arg His Leu Trp Thr Glu Thr Lys Lys Asn Asn Ile Ala Glu Lys
610                 615                 620

Glu Gly Asp Gly Ile Leu Ile Glu Phe Trp Gly Asp Leu Gln Trp Ala
625                 630                 635                 640

Phe Ala Val Ser Thr Glu Asp Arg Ser Gln Leu Val
                645                 650
```

<210> SEQ ID NO 6
<211> LENGTH: 200
<212> TYPE: PRT
<213> ORGANISM: Linum usitatissimum

<400> SEQUENCE: 6

```
Met Ser Tyr Leu Arg Asp Val Ala Thr Val Ala Leu Leu Leu Asp
1               5                   10                  15

Asn Leu Cys Cys Gly Arg Pro Asn Leu Asn Asn Asp Asn Glu Asp Thr
                20                  25                  30

Ile Gln Gln Thr Asp Ser Thr Ser Pro Val Val Asp Pro Ser Ser Ser
                35                  40                  45

Ser Gln Ser Met Asp Ser Thr Ser Val Val Asp Ala Ile Ser Asp Ser
                50                  55                  60

Thr Asn Pro Ser Ala Ser Phe Pro Ser Val Glu Tyr Asp Val Phe Leu
65              70                  75                  80

Ser Phe Arg Gly Pro Asp Thr Arg Tyr Gln Ile Thr Asp Ile Leu Tyr
                85                  90                  95
```

```
Arg Phe Leu Cys Arg Ser Lys Ile His Thr Phe Lys Asp Asp Glu
                100                 105                 110

Leu His Lys Gly Glu Glu Ile Lys Val Asn Leu Leu Arg Ala Ile Asp
            115                 120                 125

Gln Ser Lys Ile Tyr Val Pro Ile Ile Ser Arg Gly Tyr Ala Asp Ser
130                 135                 140

Lys Trp Cys Leu Met Glu Leu Ala Lys Ile Val Arg His Gln Lys Leu
145                 150                 155                 160

Asp Thr Arg Gln Ile Ile Pro Ile Phe Tyr Met Val Asp Pro Lys
                165                 170                 175

Asp Val Arg His Gln Thr Gly Pro Tyr Arg Lys Ala Phe Gln Lys His
            180                 185                 190

Ser Thr Arg Tyr Asp Glu Met Thr
            195                 200

<210> SEQ ID NO 7
<211> LENGTH: 200
<212> TYPE: PRT
<213> ORGANISM: Linum usitatissimum

<400> SEQUENCE: 7

Met Ser Tyr Leu Arg Glu Val Ala Thr Ala Val Ala Leu Leu Leu Pro
1               5                   10                  15

Phe Ile Leu Leu Asn Lys Phe Trp Arg Pro Asn Ser Lys Asp Ser Ile
                20                  25                  30

Val Asn Asp Asp Asp Ser Thr Ser Glu Val Asp Ala Ile Ser Asp
            35                  40                  45

Ser Thr Asn Pro Ser Gly Ser Phe Pro Ser Val Glu Tyr Glu Val Phe
50                  55                  60

Leu Ser Phe Arg Gly Pro Asp Thr Arg Glu Gln Phe Thr Asp Phe Leu
65                  70                  75                  80

Tyr Gln Ser Leu Arg Arg Tyr Lys Ile His Thr Phe Arg Asp Asp
                85                  90                  95

Glu Leu Leu Lys Gly Lys Glu Ile Gly Pro Asn Leu Leu Arg Ala Ile
                100                 105                 110

Asp Gln Ser Lys Ile Tyr Val Pro Ile Ile Ser Ser Gly Tyr Ala Asp
            115                 120                 125

Ser Lys Trp Cys Leu Met Glu Leu Ala Glu Ile Val Arg Arg Gln Glu
130                 135                 140

Glu Asp Pro Arg Arg Ile Ile Leu Pro Ile Phe Tyr Met Val Asp Pro
145                 150                 155                 160

Ser Asp Val Arg His Gln Thr Gly Cys Tyr Lys Lys Ala Phe Arg Lys
                165                 170                 175

His Ala Asn Lys Phe Asp Gly Thr Ile Gln Asn Trp Lys Asp Ala
            180                 185                 190

Leu Lys Lys Val Gly Asp Leu Lys
        195                 200

<210> SEQ ID NO 8
<211> LENGTH: 163
<212> TYPE: PRT
<213> ORGANISM: Nicotiana glutinosa

<400> SEQUENCE: 8

Met Ala Ser Ser Ser Ser Ser Arg Trp Ser Tyr Asp Val Phe Leu
1               5                   10                  15
```

```
Ser Phe Arg Gly Glu Asp Thr Arg Lys Thr Phe Thr Ser His Leu Tyr
            20                  25                  30

Glu Val Leu Asn Asp Lys Gly Ile Lys Thr Phe Gln Asp Asp Lys Arg
        35                  40                  45

Leu Glu Tyr Gly Ala Thr Ile Pro Gly Glu Leu Cys Lys Ala Ile Glu
    50                  55                  60

Glu Ser Gln Phe Ala Ile Val Val Phe Ser Glu Asn Tyr Ala Thr Ser
65                  70                  75                  80

Arg Trp Cys Leu Asn Glu Leu Val Lys Ile Met Glu Cys Lys Thr Arg
                85                  90                  95

Phe Lys Gln Thr Val Ile Pro Ile Phe Tyr Asp Val Asp Pro Ser His
            100                 105                 110

Val Arg Asn Gln Lys Glu Ser Phe Ala Lys Ala Phe Glu Glu His Glu
        115                 120                 125

Thr Lys Tyr Lys Asp Asp Val Glu Gly Ile Gln Arg Trp Arg Ile Ala
    130                 135                 140

Leu Asn Glu Ala Ala Asn Leu Lys Gly Ser Cys Asp Asn Arg Asp Lys
145                 150                 155                 160

Thr Asp Ala

<210> SEQ ID NO 9
<211> LENGTH: 184
<212> TYPE: PRT
<213> ORGANISM: Arabidopsis thaliana

<400> SEQUENCE: 9

Met Ala Ala Ser Ser Ser Gly Arg Arg Tyr Asp Val Phe Pro
1               5                   10                  15

Ser Phe Ser Gly Val Asp Val Arg Lys Thr Phe Leu Ser His Leu Leu
            20                  25                  30

Lys Ala Leu Asp Gly Lys Ser Ile Asn Thr Phe Ile Asp His Gly Ile
        35                  40                  45

Glu Arg Ser Arg Thr Ile Ala Pro Glu Leu Ile Ser Ala Ile Arg Glu
    50                  55                  60

Ala Arg Ile Ser Ile Val Ile Phe Ser Lys Asn Tyr Ala Ser Ser Thr
65                  70                  75                  80

Trp Cys Leu Asn Glu Leu Val Glu Ile His Lys Cys Phe Asn Asp Leu
                85                  90                  95

Gly Gln Met Val Ile Pro Val Phe Tyr Asp Val Asp Pro Ser Glu Val
            100                 105                 110

Arg Lys Gln Thr Gly Glu Phe Gly Lys Val Phe Glu Lys Thr Cys Glu
        115                 120                 125

Val Ser Lys Asp Lys Gln Pro Gly Asp Gln Lys Gln Arg Trp Val Gln
    130                 135                 140

Ala Leu Thr Asp Ile Ala Asn Ile Ala Gly Glu Asp Leu Leu Asn Gly
145                 150                 155                 160

Pro Asn Glu Ala His Met Val Glu Lys Ile Ser Asn Asp Val Ser Asn
                165                 170                 175

Lys Leu Ile Thr Arg Ser Lys Cys
            180

<210> SEQ ID NO 10
<211> LENGTH: 200
<212> TYPE: PRT
<213> ORGANISM: Arabidopsis thaliana
```

-continued

<400> SEQUENCE: 10

Met Asp Ser Ser Phe Phe Leu Val Leu Val Ala Ala Ala Thr Gly Phe
1               5                   10                  15

Phe Met Leu Phe Arg Lys Phe Arg Phe His Gln Asp Asn Lys Glu Ser
            20                  25                  30

Asn Ser Ser Ser Leu Ser Arg Pro Thr Ala Ala Thr Ser Val Ser Arg
        35                  40                  45

Asn Trp Lys His Asp Val Phe Pro Ser Phe His Gly Ala Asp Val Arg
    50                  55                  60

Arg Thr Phe Leu Ser His Ile Leu Glu Ser Phe Arg Arg Lys Gly Ile
65                  70                  75                  80

Asp Thr Phe Ile Asp Asn Asn Ile Glu Arg Ser Lys Ser Ile Gly Pro
                85                  90                  95

Glu Leu Lys Glu Ala Ile Lys Gly Ser Lys Ile Ala Ile Val Leu Leu
            100                 105                 110

Ser Arg Lys Tyr Ala Ser Ser Ser Trp Cys Leu Asp Glu Leu Ala Glu
        115                 120                 125

Ile Met Lys Cys Arg Glu Val Leu Gly Gln Ile Val Met Thr Ile Phe
130                 135                 140

Tyr Glu Val Glu Pro Thr Asp Ile Lys Lys Gln Thr Gly Glu Phe Gly
145                 150                 155                 160

Lys Ala Phe Thr Lys Thr Cys Arg Gly Lys Thr Lys Glu His Ile Glu
                165                 170                 175

Arg Trp Arg Lys Ala Leu Glu Asp Val Ala Thr Ile Ala Gly Tyr His
            180                 185                 190

Ser His Lys Trp Ser Asn Glu Ala
        195                 200

<210> SEQ ID NO 11
<211> LENGTH: 158
<212> TYPE: PRT
<213> ORGANISM: Consensus sequence constructed from alignment of M, L6,
      N, RPP5, and RPP1 TIR Domains
<220> FEATURE:
<221> NAME/KEY: MISC_FEATURE
<222> LOCATION: (2)..(2)
<223> OTHER INFORMATION: No consensus amino acid for X at this position
<220> FEATURE:
<221> NAME/KEY: MISC_FEATURE
<222> LOCATION: (3)..(3)
<223> OTHER INFORMATION: No consensus amino acid for X at this position
<220> FEATURE:
<221> NAME/KEY: MISC_FEATURE
<222> LOCATION: (4)..(4)
<223> OTHER INFORMATION: No consensus amino acid for X at this position
<220> FEATURE:
<221> NAME/KEY: MISC_FEATURE
<222> LOCATION: (5)..(5)
<223> OTHER INFORMATION: No consensus amino acid for X at this position
<220> FEATURE:
<221> NAME/KEY: MISC_FEATURE
<222> LOCATION: (6)..(6)
<223> OTHER INFORMATION: No consensus amino acid for X at this position
<220> FEATURE:
<221> NAME/KEY: MISC_FEATURE
<222> LOCATION: (8)..(8)
<223> OTHER INFORMATION: No consensus amino acid for X at this position
<220> FEATURE:
<221> NAME/KEY: MISC_FEATURE
<222> LOCATION: (9)..(9)
<223> OTHER INFORMATION: No consensus amino acid for X at this position
<220> FEATURE:
<221> NAME/KEY: MISC_FEATURE
<222> LOCATION: (12)..(12)

-continued

```
<223> OTHER INFORMATION: No consensus amino acid for X at this position
<220> FEATURE:
<221> NAME/KEY: MISC_FEATURE
<222> LOCATION: (17)..(17)
<223> OTHER INFORMATION: No consensus amino acid for X at this position
<220> FEATURE:
<221> NAME/KEY: MISC_FEATURE
<222> LOCATION: (18)..(18)
<223> OTHER INFORMATION: No consensus amino acid for X at this position
<220> FEATURE:
<221> NAME/KEY: MISC_FEATURE
<222> LOCATION: (19)..(19)
<223> OTHER INFORMATION: No consensus amino acid for X at this position
<220> FEATURE:
<221> NAME/KEY: MISC_FEATURE
<222> LOCATION: (20)..(20)
<223> OTHER INFORMATION: No consensus amino acid for X at this position
<220> FEATURE:
<221> NAME/KEY: MISC_FEATURE
<222> LOCATION: (30)..(30)
<223> OTHER INFORMATION: No consensus amino acid for X at this position
<220> FEATURE:
<221> NAME/KEY: MISC_FEATURE
<222> LOCATION: (34)..(34)
<223> OTHER INFORMATION: No consensus amino acid for X at this position
<220> FEATURE:
<221> NAME/KEY: MISC_FEATURE
<222> LOCATION: (42)..(42)
<223> OTHER INFORMATION: No consensus amino acid for X at this position
<220> FEATURE:
<221> NAME/KEY: MISC_FEATURE
<222> LOCATION: (43)..(43)
<223> OTHER INFORMATION: No consensus amino acid for X at this position
<220> FEATURE:
<221> NAME/KEY: MISC_FEATURE
<222> LOCATION: (45)..(45)
<223> OTHER INFORMATION: No consensus amino acid for X at this position
<220> FEATURE:
<221> NAME/KEY: MISC_FEATURE
<222> LOCATION: (48)..(48)
<223> OTHER INFORMATION: No consensus amino acid for X at this position
<220> FEATURE:
<221> NAME/KEY: MISC_FEATURE
<222> LOCATION: (52)..(52)
<223> OTHER INFORMATION: No consensus amino acid for X at this position
<220> FEATURE:
<221> NAME/KEY: MISC_FEATURE
<222> LOCATION: (55)..(55)
<223> OTHER INFORMATION: No consensus amino acid for X at this position
<220> FEATURE:
<221> NAME/KEY: MISC_FEATURE
<222> LOCATION: (56)..(56)
<223> OTHER INFORMATION: No consensus amino acid for X at this position
<220> FEATURE:
<221> NAME/KEY: MISC_FEATURE
<222> LOCATION: (59)..(59)
<223> OTHER INFORMATION: No consensus amino acid for X at this position
<220> FEATURE:
<221> NAME/KEY: MISC_FEATURE
<222> LOCATION: (61)..(61)
<223> OTHER INFORMATION: No consensus amino acid for X at this position
<220> FEATURE:
<221> NAME/KEY: MISC_FEATURE
<222> LOCATION: (62)..(62)
<223> OTHER INFORMATION: No consensus amino acid for X at this position
<220> FEATURE:
<221> NAME/KEY: MISC_FEATURE
<222> LOCATION: (64)..(64)
<223> OTHER INFORMATION: No consensus amino acid for X at this position
<220> FEATURE:
<221> NAME/KEY: MISC_FEATURE
<222> LOCATION: (68)..(68)
<223> OTHER INFORMATION: No consensus amino acid for X at this position
<220> FEATURE:
<221> NAME/KEY: MISC_FEATURE
<222> LOCATION: (69)..(69)
<223> OTHER INFORMATION: No consensus amino acid for X at this position
<220> FEATURE:
<221> NAME/KEY: MISC_FEATURE
```

```
<222> LOCATION: (72)..(72)
<223> OTHER INFORMATION: No consensus amino acid for X at this position
<220> FEATURE:
<221> NAME/KEY: MISC_FEATURE
<222> LOCATION: (73)..(73)
<223> OTHER INFORMATION: No consensus amino acid for X at this position
<220> FEATURE:
<221> NAME/KEY: MISC_FEATURE
<222> LOCATION: (77)..(77)
<223> OTHER INFORMATION: No consensus amino acid for X at this position
<220> FEATURE:
<221> NAME/KEY: MISC_FEATURE
<222> LOCATION: (81)..(81)
<223> OTHER INFORMATION: No consensus amino acid for X at this position
<220> FEATURE:
<221> NAME/KEY: MISC_FEATURE
<222> LOCATION: (83)..(83)
<223> OTHER INFORMATION: No consensus amino acid for X at this position
<220> FEATURE:
<221> NAME/KEY: MISC_FEATURE
<222> LOCATION: (84)..(84)
<223> OTHER INFORMATION: No consensus amino acid for X at this position
<220> FEATURE:
<221> NAME/KEY: MISC_FEATURE
<222> LOCATION: (87)..(87)
<223> OTHER INFORMATION: No consensus amino acid for X at this position
<220> FEATURE:
<221> NAME/KEY: MISC_FEATURE
<222> LOCATION: (89)..(89)
<223> OTHER INFORMATION: No consensus amino acid for X at this position
<220> FEATURE:
<221> NAME/KEY: MISC_FEATURE
<222> LOCATION: (93)..(93)
<223> OTHER INFORMATION: No consensus amino acid for X at this position
<220> FEATURE:
<221> NAME/KEY: MISC_FEATURE
<222> LOCATION: (99)..(99)
<223> OTHER INFORMATION: No consensus amino acid for X at this position
<220> FEATURE:
<221> NAME/KEY: MISC_FEATURE
<222> LOCATION: (100)..(100)
<223> OTHER INFORMATION: No consensus amino acid for X at this position
<220> FEATURE:
<221> NAME/KEY: MISC_FEATURE
<222> LOCATION: (102)..(102)
<223> OTHER INFORMATION: No consensus amino acid for X at this position
<220> FEATURE:
<221> NAME/KEY: MISC_FEATURE
<222> LOCATION: (103)..(103)
<223> OTHER INFORMATION: No consensus amino acid for X at this position
<220> FEATURE:
<221> NAME/KEY: MISC_FEATURE
<222> LOCATION: (104)..(104)
<223> OTHER INFORMATION: No consensus amino acid for X at this position
<220> FEATURE:
<221> NAME/KEY: MISC_FEATURE
<222> LOCATION: (106)..(106)
<223> OTHER INFORMATION: No consensus amino acid for X at this position
<220> FEATURE:
<221> NAME/KEY: MISC_FEATURE
<222> LOCATION: (107)..(107)
<223> OTHER INFORMATION: No consensus amino acid for X at this position
<220> FEATURE:
<221> NAME/KEY: MISC_FEATURE
<222> LOCATION: (111)..(111)
<223> OTHER INFORMATION: No consensus amino acid for X at this position
<220> FEATURE:
<221> NAME/KEY: MISC_FEATURE
<222> LOCATION: (113)..(113)
<223> OTHER INFORMATION: No consensus amino acid for X at this position
<220> FEATURE:
<221> NAME/KEY: MISC_FEATURE
<222> LOCATION: (117)..(117)
<223> OTHER INFORMATION: No consensus amino acid for X at this position
<220> FEATURE:
<221> NAME/KEY: MISC_FEATURE
<222> LOCATION: (119)..(119)
<223> OTHER INFORMATION: No consensus amino acid for X at this position
<220> FEATURE:
```

```
<221> NAME/KEY: MISC_FEATURE
<222> LOCATION: (120)..(120)
<223> OTHER INFORMATION: No consensus amino acid for X at this position
<220> FEATURE:
<221> NAME/KEY: MISC_FEATURE
<222> LOCATION: (121)..(121)
<223> OTHER INFORMATION: No consensus amino acid for X at this position
<220> FEATURE:
<221> NAME/KEY: MISC_FEATURE
<222> LOCATION: (122)..(122)
<223> OTHER INFORMATION: No consensus amino acid for X at this position
<220> FEATURE:
<221> NAME/KEY: MISC_FEATURE
<222> LOCATION: (123)..(123)
<223> OTHER INFORMATION: No consensus amino acid for X at this position
<220> FEATURE:
<221> NAME/KEY: MISC_FEATURE
<222> LOCATION: (125)..(125)
<223> OTHER INFORMATION: No consensus amino acid for X at this position
<220> FEATURE:
<221> NAME/KEY: MISC_FEATURE
<222> LOCATION: (127)..(127)
<223> OTHER INFORMATION: No consensus amino acid for X at this position
<220> FEATURE:
<221> NAME/KEY: MISC_FEATURE
<222> LOCATION: (129)..(129)
<223> OTHER INFORMATION: No consensus amino acid for X at this position
<220> FEATURE:
<221> NAME/KEY: MISC_FEATURE
<222> LOCATION: (130)..(130)
<223> OTHER INFORMATION: No consensus amino acid for X at this position
<220> FEATURE:
<221> NAME/KEY: MISC_FEATURE
<222> LOCATION: (131)..(131)
<223> OTHER INFORMATION: No consensus amino acid for X at this position
<220> FEATURE:
<221> NAME/KEY: MISC_FEATURE
<222> LOCATION: (134)..(134)
<223> OTHER INFORMATION: No consensus amino acid for X at this position
<220> FEATURE:
<221> NAME/KEY: MISC_FEATURE
<222> LOCATION: (137)..(137)
<223> OTHER INFORMATION: No consensus amino acid for X at this position
<220> FEATURE:
<221> NAME/KEY: MISC_FEATURE
<222> LOCATION: (138)..(138)
<223> OTHER INFORMATION: No consensus amino acid for X at this position
<220> FEATURE:
<221> NAME/KEY: MISC_FEATURE
<222> LOCATION: (141)..(141)
<223> OTHER INFORMATION: No consensus amino acid for X at this position
<220> FEATURE:
<221> NAME/KEY: MISC_FEATURE
<222> LOCATION: (142)..(142)
<223> OTHER INFORMATION: No consensus amino acid for X at this position
<220> FEATURE:
<221> NAME/KEY: MISC_FEATURE
<222> LOCATION: (143)..(143)
<223> OTHER INFORMATION: No consensus amino acid for X at this position
<220> FEATURE:
<221> NAME/KEY: MISC_FEATURE
<222> LOCATION: (144)..(144)
<223> OTHER INFORMATION: No consensus amino acid for X at this position
<220> FEATURE:
<221> NAME/KEY: MISC_FEATURE
<222> LOCATION: (145)..(145)
<223> OTHER INFORMATION: No consensus amino acid for X at this position
<220> FEATURE:
<221> NAME/KEY: MISC_FEATURE
<222> LOCATION: (146)..(146)
<223> OTHER INFORMATION: No consensus amino acid for X at this position
<220> FEATURE:
<221> NAME/KEY: MISC_FEATURE
<222> LOCATION: (147)..(147)
<223> OTHER INFORMATION: No consensus amino acid for X at this position
<220> FEATURE:
<221> NAME/KEY: MISC_FEATURE
<222> LOCATION: (149)..(149)
<223> OTHER INFORMATION: No consensus amino acid for X at this position
```

```
<220> FEATURE:
<221> NAME/KEY: MISC_FEATURE
<222> LOCATION: (150)..(150)
<223> OTHER INFORMATION: No consensus amino acid for X at this position
<220> FEATURE:
<221> NAME/KEY: MISC_FEATURE
<222> LOCATION: (151)..(151)
<223> OTHER INFORMATION: No consensus amino acid for X at this position
<220> FEATURE:
<221> NAME/KEY: MISC_FEATURE
<222> LOCATION: (152)..(152)
<223> OTHER INFORMATION: No consensus amino acid for X at this position
<220> FEATURE:
<221> NAME/KEY: MISC_FEATURE
<222> LOCATION: (153)..(153)
<223> OTHER INFORMATION: No consensus amino acid for X at this position
<220> FEATURE:
<221> NAME/KEY: MISC_FEATURE
<222> LOCATION: (154)..(154)
<223> OTHER INFORMATION: No consensus amino acid for X at this position
<220> FEATURE:
<221> NAME/KEY: MISC_FEATURE
<222> LOCATION: (155)..(155)
<223> OTHER INFORMATION: No consensus amino acid for X at this position
<220> FEATURE:
<221> NAME/KEY: MISC_FEATURE
<222> LOCATION: (156)..(156)
<223> OTHER INFORMATION: No consensus amino acid for X at this position
<220> FEATURE:
<221> NAME/KEY: MISC_FEATURE
<222> LOCATION: (157)..(157)
<223> OTHER INFORMATION: No consensus amino acid for X at this position

<400> SEQUENCE: 11

Ser Xaa Xaa Xaa Xaa Xaa Ser Xaa Xaa Thr Ala Xaa Ser Ser Ser Ser
1               5                   10                  15

Xaa Xaa Xaa Xaa Tyr Asp Val Phe Leu Ser Phe Arg Gly Xaa Asp Thr
            20                  25                  30

Arg Xaa Thr Phe Thr Ser His Leu Tyr Xaa Xaa Leu Xaa Arg Lys Xaa
        35                  40                  45

Ile Thr Phe Xaa Asp Asp Xaa Xaa Leu Glu Xaa Gly Xaa Xaa Ile Xaa
    50                  55                  60

Pro Glu Leu Xaa Xaa Ala Ile Xaa Xaa Ser Lys Ile Xaa Ile Val Ile
65                  70                  75                  80

Xaa Ser Xaa Xaa Tyr Ala Xaa Ser Xaa Trp Cys Leu Xaa Glu Leu Ala
            85                  90                  95

Glu Ile Xaa Xaa Cys Xaa Xaa Xaa Asp Xaa Xaa Gln Thr Gly Xaa Phe
            100                 105                 110

Xaa Lys Ala Phe Xaa Lys Xaa Xaa Xaa Xaa Lys Xaa Lys Xaa Asp
        115                 120                 125

Xaa Xaa Xaa Ile Gln Xaa Arg Trp Xaa Xaa Ala Leu Xaa Xaa Xaa Ala
        130                 135                 140

Xaa Xaa Xaa Gly Xaa Xaa Xaa Xaa Xaa Xaa Xaa Ala
145                 150                 155
```

TRANSGENIC PLANTS HAVING NON-PATHOGEN INDUCED SYSTEMIC ACQUIRED RESISTANCE (SAR)

CROSS-REFERENCE TO RELATED APPLICATIONS

This application claims the benefit of U.S. Provisional Application No. 60/191,027, filed Mar. 21, 2000; herein incorporated by reference.

FIELD OF THE INVENTION

This invention relates to nucleic acid molecules useful for producing plants having enhanced pathogen resistance characteristics, transgenic plants expressing these nucleic acid molecules, methods of making such plants, and methods for increasing the resistance of plants to pathogens.

BACKGROUND OF THE INVENTION

Plants are hosts to thousands of infectious diseases caused by a vast array of phytopathogenic fungi, bacteria, viruses, and nematodes. These pathogens are responsible for significant crop losses worldwide, resulting from both infection of growing plants and destruction of harvested crops (Baker et al., 1997).

Plants recognize and resist many invading phytopathogens by inducing a rapid defense response, termed the hypersensitive response (HR). HR results in localized cell and tissue death at the site of infection, which constrains further spread of the infection. This local response often triggers non-specific resistance throughout the plant, a phenomenon known as systemic acquired resistance (SAR). Once triggered, SAR provides resistance for days to a wide range of pathogens. The generation of the HR and SAR in a plant depends upon the interaction between a dominant or semi-dominant resistance (R) gene product in the plant and a corresponding dominant avirulence (Avr) gene product expressed by the invading phytopathogen. It has been proposed that phytopathogen Avr products function as ligands, and that plant R products function as receptors. Thus, in the widely accepted model of phytopathogen/plant interaction, binding of the Avr product of an invading pathogen to a corresponding R product in the plant initiates the chain of events within the plant that produces HR and SAR and ultimately leads to disease resistance. A detailed review of the current understanding of Avr/R gene product interactions is presented in Baker et al. (1997).

Because the systemic acquired resistance (SAR) response acts nonspecifically throughout the plant to provide enhanced resistance to many pathogens, it has been extensively studied as a possible mechanism for conferring broad-spectrum pathogen resistance. The SAR response is characterized by the induction of at least nine gene families (known as SAR genes) in uninfected leaves of the plant. Some of the SAR genes encode proteins that have antimicrobial activity, including glucanases, chitinases and the pathogenesis-related (PR) proteins such as PR-1. A number of chemicals are known to trigger SAR, including salicylic acid, 2,6-dichloroisonicotinic acid (INA), 1,2,3-benzothiadiazole-7-thiocarboxylic acid-S-methyl ester, and arachidonic acid when applied through the roots, sprayed onto leaves or injected into stems. These and other chemicals are being investigated as candidate agents for inducing SAR in crop plants on an agricultural scale. For a more detailed discussion of the SAR response, see Agrios (1997), Chapter 5.

While efforts to utilize the SAR response to enhance resistance to phytopathogens have largely been based on the external application of inducing agents, molecular genetic research has focused on isolating and manipulating plant resistance (R) genes. Since the cloning of the first R gene, Pto from tomato, which confers resistance to *Pseudomonas syringae* pv. tomato (Martin et al., 1993), a number of other R genes have been reported (for reviews see Hammond-Kosack and Jones, 1997 and Baker et al., 1997). Sequence analyses of the proteins encoded by these R genes have revealed a number of motifs that are conserved between various R proteins; including leucine rich repeats (LRR), nucleotide binding site (NBS), Toll-IL-1R homology (TIR), leucine zipper (LZ) and transmembrane (TM) domains (Baker et al., 1997).

Much effort is currently being directed towards using R genes to engineer pathogen resistance in plants. The production of transgenic plants carrying a heterologous gene sequence is now routinely practiced by plant molecular biologists, and methods for incorporating an isolated gene (such as an R gene) into an expression cassette, producing plant transformation vectors, and transforming many types of plants are well known. Examples of the production of transgenic plants having modified characteristics as a result of the introduction of a heterologous transgene include: U.S. Pat. No. 5,719,046 to Guerineau (production of herbicide resistant plants by introduction of bacterial dihydropteroate synthase gene); U.S. Pat. No. 5,231,020 to Jorgensen (modification of flavenoids in plants); U.S. Pat. No. 5,583,021 to Dougherty (production of virus resistant plants); and U.S. Pat. No. 5,767,372 to De Greve and U.S. Pat. No. 5,500,365 to Fischoff (production of insect resistant plants by introducing *Bacillus thuringiensis* genes).

In conjunction with such techniques, the isolation of plant R genes has similarly permitted the production of plants having enhanced resistance to certain pathogens. A number of these genes have been used to introduce the encoded resistance characteristic into plant lines that were previously susceptible to the corresponding pathogen. For example, U.S. Pat. No. 5,571,706 to Baker and Whitham describes the introduction of the N gene into tobacco lines that are susceptible to Tobacco Mosaic Virus (TMV) in order to produce TMV-resistant tobacco plants. WO 95/28423 describes the creation of transgenic plants carrying the Rps2 gene from *Arabidopsis thaliana*, as a means of creating resistance to bacterial pathogens including *Pseudomonas syringae*, and WO 98/02545 describes the introduction of the Prf gene into plants to obtain enhanced pathogen resistance. Cao et al. (1998) describes the introduction into Arabidopsis of the NPR1 cDNA expressed under the control of the 35S promoter to produce enhanced resistance to multiple bacterial pathogens.

The first R gene conferring virus resistance to be isolated from plants was the N gene of *Nicotiana glutinosa* tobacco (Whitham et al., 1994). The N gene (or homologs of this gene) is present in some but not all types of tobacco, and confers resistance to Tobacco Mosaic Virus (TMV). TMV is an important pathogen of not only tobacco, but also of other crop plants including tomato (Lycopersicon sp.) and pepper (Capsicum sp.). A review of the wide range of host species that serve as hosts to TMV is presented in Holmes (1946). TMV is the type virus of the genus Tobamovirus, which includes a number of closely related viral pathogens of commercially important plants. For example, the Tobamovirus group includes tomato mosaic virus, pepper green mottle virus and ondontoglossum ringspot virus, which is a pathogen of orchids (Agrios, 1997).

The *N. glutinosa* N gene is described in detail in U.S. Pat. No. 5,571,706 ("Plant Virus Resistance Gene and Methods")

to Baker & Whitham, which is incorporated herein by reference. The sequence of this gene is available on GenBank under accession number U558886. U.S. Pat. No. 5,571,706 discloses the sequence of the N gene, as well as two cDNAs corresponding to the gene. The N gene (including the 5' and 3' regulatory regions) is over 12 kb in length and comprises five exons and four introns, encoding a full-length N protein of 1144 amino acids, with a deduced molecular mass of 131.4 kDa. cDNA-N is a cDNA encoded by the N gene; it is approximately 3.7 kb in length and encodes the full-length N protein. A second cDNA, cDNA-N-tr, is approximately 3.8 kb in length. It results from an alternative splicing pattern and encodes a truncated protein, N-tr, that is 652 amino acids in length and has a deduced molecular mass of 75.3 kDa. The N protein include TIR, NBS and LRR domains (Whitham et al., 1994, Baker et al., 1997). U.S. Pat. No. 5,571,706, and Whitham et al. (1994) describe the production of transgenic tobacco plants carrying a full-length N transgene; these plants show the HR response following TMV challenge.

While molecular genetic approaches that focus on individual R genes are promising, such approaches may be somewhat limited since each individual R gene will likely confer resistance to a relatively narrow range of pathogens. In contrast, exploitation of the SAR response could produce plants that are resistant to a broad range of pathogens of different types. The present invention is directed to a molecular genetic approach for producing plants that display an SAR response even in the absence of a plant pathogen, and which consequently show enhanced resistance to a broad spectrum of plant pathogens.

SUMMARY OF THE INVENTION

A molecular-genetic approach for producing a constitutive systemic acquired resistance (SAR) response in plants is provided. The SAR response in these plants is described as "constitutive" since it occurs even in the absence of an infecting pathogen. Plants that exhibit this SAR response show enhanced resistance to a broad range of phytopathogens, including viruses such as TMV, bacteria and fungi. Among other things, the invention encompasses nucleic acid molecules that are used to produce plants that show such an SAR response, the plants themselves and methods of making such plants.

The invention is founded on the discovery that a non-pathogen induced SAR response is exhibited by transgenic plants that comprise the following elements:

(1) an R gene (or a cDNA encoding the R gene product(s)); and (2) a transgene that expresses the R gene product (or an effective portion thereof).

Typically, element (1) is a native R gene, but it may also be a transgene comprising the R gene, a corresponding R cDNA, or a recombinant construct that otherwise expresses the R protein(s). (As described in more detail below, while most R genes have only a single reading frame and therefore encode a single R protein product, some R genes, including the tobacco N gene and the flax L6 gene, contain alternatively spliced exons, and therefore encode two R protein products.) The nucleic acid molecule of element (1) is, by itself, ordinarily sufficient to confer enhanced resistance to a pathogen that carries the corresponding Avr gene when expressed in an otherwise susceptible plant. Expression of this nucleic acid molecule is typically, but not necessarily, controlled by regulatory elements (promoter and terminator regions) that are associated with the native R gene.

Element (2) is typically a cDNA form of the R gene, and is generally expressed in the plant under the control of a promoter that produces expression levels that are greater than the native R gene promoter. High-level promoters suitable for use in this application are well known in the art, and include inducible and constitutive promoters. Inducible promoters may be employed in situations where it is advantageous to control expression of the non-pathogen induced SAR response. For example, it may be beneficial to turn on the SAR response once plants have reached a certain developmental stage, or when the likelihood of pathogen infection is highest. As described in more detail below, element (2) need not necessarily encode a complete R gene product but, in some circumstances, may encode only a portion of the R protein. The inventors have shown, for example, that element (2) may encode one or more domains of an R protein, but need not encode a complete R protein. For example, in certain embodiments, element (2) may encode all or part of a TIR domain of an R protein.

R genes and R gene products that may be employed in the invention include, but are not limited to, R genes encoding proteins having a TIR domain, such as: the N gene of tobacco (described in U.S. Pat. No. 5,571,706); the RPP5 gene of Arabidopsis (described in Parker et al., 1997) the RPP1 gene of Arabidopsis (described in Botella et al., 1998); the L6 gene of flax (described in Lawrence et al., 1995); and the M gene of flax (described in Anderson et al., 1997). Transgenic plants produced according to the invention (referred to as constitutive SAR plants for convenience) exhibit an SAR response and, as a result, shown enhanced resistance to a wide range of pathogens, including bacterial, viral and fungal pathogens.

In one embodiment of the invention, the invention provides transgenic plants comprising:

(1) a first nucleic acid molecule encoding one or more protein products of an R gene sufficient to confer resistance to a phytopathogen; and (2) a second nucleic acid molecule encoding a protein comprising at least one polypeptide encoded by the R gene, wherein co-expression of the first and second nucleic acid molecules is sufficient to produce a systemic acquired resistance response in the plant.

The term "a protein comprising at least one polypeptide encoded by the R gene" refers to a protein that includes at least one amino acid region (typically at least 10 contiguous amino acids) of the R protein. In other words, the polypeptide may be a sub-part of the R protein. Typically, such a polypeptide will be a domain of the R protein, such as a TIR domain, although less than an entire domain may also be employed.

The invention also encompasses a method of producing a plant that exhibits an SAR response in the absence of a pathogen infection. The method comprises introducing into a plant having an R gene a nucleic acid molecule that expresses a polypeptide component of a protein encoded by the R gene, wherein co-expression of the R gene and the polypeptide component produces an SAR response in the plant.

In another embodiment, the invention provides transgenic plants comprising a first nucleic acid molecule encoding an R gene product having a TIR domain, and a second nucleic acid molecule encoding a polypeptide comprising the TIR domain of the R gene product or an effective portion thereof, wherein co-expression of the first and second nucleic acid molecules produces a constitutive SAR response in the plant. In particular cases, the R gene product may be a product of a gene selected from the group consisting of the N gene of tobacco, the M and L6 genes of flax and the RPP5 and RPP1 genes of Arabidopsis.

In another embodiment of the invention, the R gene is the tobacco N gene, and the transgenic plants comprise the following elements:

(1) a first nucleic acid molecule encoding an N and an N-tr protein; and (2) a second nucleic acid molecule encoding a protein comprising an N protein TIR domain.

The first nucleic acid molecule may be any molecule that encodes an N protein and an N-tr protein. Thus, for example, the first nucleic acid molecule may be a native N gene, an N transgene, or a cDNA-N/intron construct.

In one embodiment, the second nucleic acid molecule comprises cDNA-N or cDNA-N-tr. In another embodiment, the second nucleic acid molecule comprises a recombinant molecule encoding the N protein TIR region or a sufficient part of the TIR region to produce the SAR response when the first and second nucleic acid molecules are co-expressed in the plant.

Plants produced by the methods disclosed herein exhibit a constitutive SAR response and, consequently, enhanced broad-spectrum pathogen resistance. Parts of such plants, including seeds, fruit, stems, leaves and roots, may be utilized in conventional ways as food sources etc. The present invention is applicable to any plant type, but is expected to be particularly useful in plant types from which the corresponding R gene is obtained, and closely related plants. By way of example, application of the invention based on the tobacco N gene is expected to be particularly beneficial with respect to solanaceaous plants such as tobacco, tomato, potato and pepper.

The invention also encompasses methods for increasing or enhancing the disease resistance of plants. Such methods for increasing the disease resistance of plants involve plants having a first and second nucleic acid molecule as described supra. The methods comprise obtaining a plant having a first nucleic acid molecule encoding one or more protein products of an R gene sufficient to confer resistance to a phytopathogen; and then introducing into the genome of said plant a second nucleic acid molecule comprising at least one polypeptide encoded by the R gene, wherein co-expression of the first and second nucleic acid molecules is sufficient to produce a systemic acquired resistance response in the plant. The R gene of the first nucleic acid molecule can be native to the plant or can be introduced into the genome of the plant that lacks the R gene.

BRIEF DESCRIPTION OF THE DRAWINGS

FIG. 1 shows an alignment of the TIR domains of N (SEQ ID NO: 8), M (SEQ ID NO: 6), L6 (SEQ ID NO: 7), RPP5 (SEQ ID NO: 9), and RPP1 (SEQ ID NO: 10). The consensus sequence (SEQ ID NO: 11) (the lower line of the figure) represents amino acids that are conserved between 3 or more of the 5 proteins.

FIG. 3 shows the constitutive HR phenotype in TIR::Samsun NN transgenic plants overexpressing TIR after 8–10 weeks; expression occurred in the absence of TMV infection.

DETAILED DESCRIPTION OF THE INVENTION

I. Sequence Listing

Figure 2:
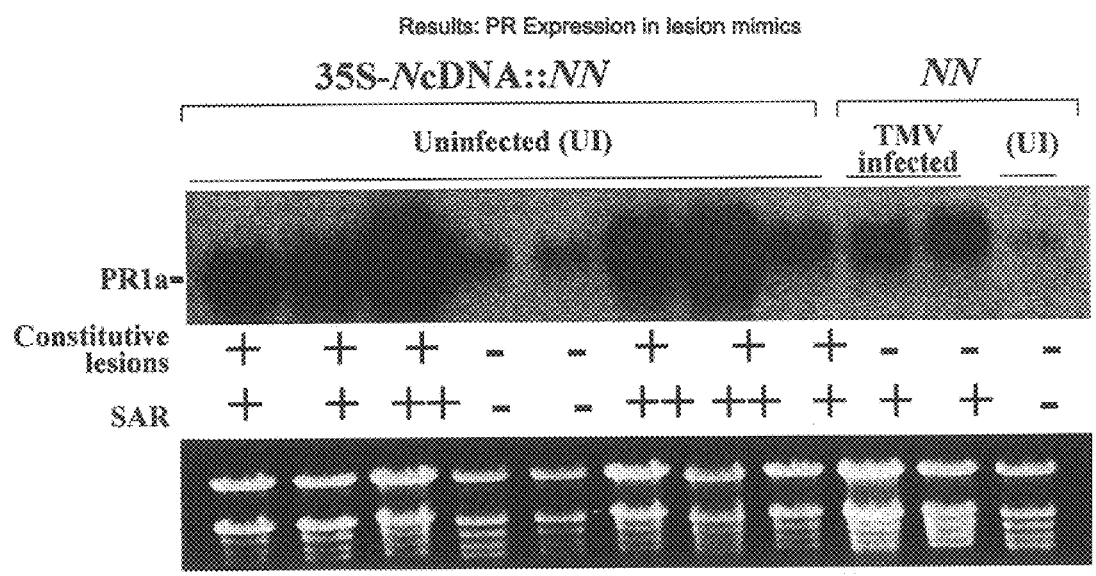
FIG. 2 is a composite figure showing data obtained with lesion mimic plants. The data shows Northern blot analyses of PR-1a expression, and the presence or absence of constitutive lesions and SAR response (the lower panel shows ribosomal RNA staining showing the even loading of RNA gels). Eight lines of NN tobacco transformed with the 35S-cDNA-N construct are shown. The phenotype observations and RNA collection from these samples were performed in the absence of TMV infection. The right-hand three lanes represent analyses of non-transgenic NN plants. The first two of these were infected with TMV approximately 10 days prior to sampling, the last was not infected. I=infected with TMV, U.I.=uninfected.

SEQ ID NO:1 shows the nucleic acid sequence of the *N. glutinosa* N gene. The sequence comprises the following regions:

| Nucleotide numbers | Feature |
| --- | --- |
| 1–4281 | 5' regulatory sequence (pN) |
| 4282–4760 | exon 1 (last codon split between exon 1 and exon 2) |
| 4761–4990 | intron 1 |
| 4991–6086 | exon 2 |
| 6087–6928 | intron 2 |
| 6929–7201 | exon 3 |
| 7202–9019 | intron 3 |
| 9020–10588 | exon 4 |
| 10589–10921 | intron 4 |
| 10922–10939 | exon 5 |
| 10940–12286 | 3' regulatory region (3'-GRS) |

SEQ ID NO:2 shows the nucleic acid sequence of the *N. glutinosa* cDNA-N.

SEQ ID NO:3 shows the amino acid sequence of the *N. glutinosa* N protein.

SEQ ID NO:4 shows the nucleic acid sequence of the *N. glutinosa* cDNA-N-tr.

SEQ ID NO:5 shows the amino acid sequence of the *N. glutinosa* N-tr protein.

II. Definitions

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following definitions of terms are provided:

R gene: A plant disease resistance gene which, when expressed in a plant, confers enhanced resistance to one or more phytopathogens. R genes typically encode one or more R proteins, the production of which is required for pathogen resistance. In the gene-for-gene model of plant disease resistance, R genes provide resistance against pathogens that carry a corresponding avirulence (Avr) gene. Examples of plant R genes include, but are not limited to, those shown in Table 1.

TABLE 1

Examples of cloned R genes

| R Gene | Isolated from | Confers resistance to | Conserved domains | Citation |
|---|---|---|---|---|
| N | tobacco | TMV | TIR-NBS-LRR | Whitham et al. (1994) |
| Hm1 | maize | *Cochliobolus carbonum* | — | Johal and Briggs (1992) |
| Pto | tomato | *Pseudomonas syringae* pv. tomato | — | Martin et al. (1993) |
| RPS2 | Arabidopsis | *Pseudomonas syringae* pv. tomato | LZ-NBS-LRR | Bent et al. (1994) |
| RPM1 | Arabidopsis | *Pseudomonas syringae* pv. maculicula | LZ-NBS-LRR | Grant et al. (1995) |
| $I_2$ | tomato | *Fusarium oxysporum* | NBS-LRR | Ori et al. (1997) |
| M | flax | *Melampsora lini* | TIR-NBS-LRR | Anderson et al. (1997) |
| L6 | flax | *Melampsora lini* | TIR-NBS-LRR | Lawrence et al. (1995) |
| RPP1 | Arabidopsis | *Peronospora parasitica* | TIR-NBS-LRR | Botella et al. (1998) |
| RPP5 | Arabidopsis | *Peronospora parasitica* | TIR-NBS-LRR | Parker et al. (1997) |
| Xa21 | rice | *Xanthamonas oryzae* pv. *oryzae* | LRR | Song et al. (1995) |
| Cf2 | tomato | *Cladosporium fulvum* | LRR-TM | Dixon et al. (1995) |
| Cf9 | tomato | *Cladosporium fulvum* | LRR-TM | Jones et al. (1994) |
| HSI[pro-1] | sugar beet | *Heterodera schachtii* | LRR-TM | Cal et al. (1997) |

Detailed descriptions of these and other R genes are presented in Hammond-Kosack and Jones, 1996, Baker et al., 1997, and references cited therein.

The various R gene sequences known in the art may be regarded as prototypical sequences; homologs or variants of each of these sequences may be isolated or produced by recombinant means and used in the present invention. Such homologous and variant R genes encode homologous and variant R proteins that share specified levels of sequence identity with the relevant prototypical R gene sequence and retain R gene function. By way of example, R gene homologs and variants typically encode R proteins that share at least 40% sequence identity with the relevant prototypical R protein, and confer enhanced disease resistance when expressed in an otherwise pathogen-susceptible host plant. By way of example, variants or homologs of the prototypical flax L6 gene disclosed in Lawrence et al. (1995) will encode an L6 protein that shares at least 40% amino acid sequence identity with the prototypical L6 protein, and retain L6 gene function, i.e., retain the ability to confer enhanced resistance to the pathogen *Melampsora lini* when expressed in otherwise susceptible flax plants.

In view of this, it will be apparent to one of ordinary skill in the art that the invention is not limited to use of the prototypical R gene sequences, but that it may be practiced using variants and homologs of the sequences. Accordingly, where reference is made herein to molecules relating to an R gene, for example the flax L6 gene, the L6 cDNA or the L6 protein, it will be understood that such reference includes not only the prototypical sequences of these molecules as reported in the scientific literature, but also corresponding sequences of L6 gene homologs and variants. Also included within the scope of such terms are molecules that differ from the disclosed prototypical molecules by minor variations, such as nucleic acid molecules that vary from the disclosed sequences by virtue of the degeneracy of the genetic code, and nucleic acid sequences that have been modified to encode R proteins having conservative amino acid substitutions. Such variant sequences may be produced by manipulating the nucleotide sequence of a selected prototypical R gene using standard procedures such as site-directed mutagenesis or the polymerase chain reaction.

R protein: a protein encoded by an R gene. While most R genes encode a single protein, some R genes, including N and L6, show alternative splicing patterns, producing two mRNAs that are translatable into two different (but closely related) R proteins (see Whithamn et al., 1994; Parker et al., 1997). Expression in a plant of the R protein(s) encoded by an R gene produces resistance to pathogens carrying the corresponding Avr gene.

cDNA-R: a cDNA molecule that encodes an R protein.

TIR domain: The amino terminus of certain R proteins, including the proteins encoded by the N gene of tobacco, the M and L6 genes of flax and the RPP5 and RPP1 genes of Arabidopsis, contain a region that shows similarity to the cytoplasmic domains of the Drosophila Toll protein (amino acids 848–999) and human IL-1R protein (amino acids 352–527) (Hammond-Kosack and Jones, 1996; Whitham et al., 1994; Baker et al., 1997; Parker et al., 1997). The TIR domain has been suggested to be associated with a signaling function. The TIR domain of R genes is defined by sequence similarity (see, for example, Hammond-Kosack et al., 1997) and is generally found in the first approximately 150 amino acids of the amino terminus of the protein. FIG. 1 shows an alignment of the TIR domains of N, M, L6, RPP5 and RPP1. The consensus sequence (the lower line of the figure) represents amino acids that are conserved between 3 or more of the 5 proteins. Table 2 below shows the percentage sequence similarities and identities of the TIR regions of 4 R genes using the N gene as the reference sequence. The first 150 N-terminal amino acids of each R protein were compared for this analysis. The percentages were obtained by comparing the sequences with the GCG software package (GCG version 9, Genetics Computer Group, Madison, Wis., a subsidiary of Oxford Molecular Group, Inc.) using the Bestfit alignment set to default parameters (gap creation penalty=12, gap extension penalty=4). Typically, an R protein TIR region will have at least 45% sequence similarity to the N protein TIR region when compared using this method.

TABLE 2

Percentage similarity/identity of TIR domains to the N TIR domain

| N | RPP5 | L6 | M | RPP1 |
|---|---|---|---|---|
| 100/100 | 57/53 | 53/43 | 55/46 | 53/44 |

Systemic Acquired Resistance (SAR): SAR is a non-specific defense response of plants that is usually triggered following the induction of a hypersensitive response (HR; localized necrotic lesions around the site of a pathogen infection) by an invading pathogen. SAR has been observed in both monocotyledenous and dicotyledenous plants and may be triggered by any type of invading pathogen (bacteria, virus or fungus). The SAR response is non-specific in that it produces enhanced resistance to a broad spectrum of pathogens, regardless of the type of invading pathogen that triggered the response. It generally occurs throughout the plant, regardless of where the pathogen infection occurred. The SAR response usually begins within 2–10 days after the triggering pathogen invasion, and lasts for anywhere from several days to several weeks.

The SAR response is typically characterized at the molecular level by the induction of families of genes termed SAR genes. These genes encode products including glucanases, chitinases, csyteine-rich proteins related to thaumatin and pathogenesis-related (PR) proteins. For a more detailed discussion of the SAR response, see Agrios et al. (1997), Chapter 5, and Ryals et al. (1994). Methods for detecting the SAR response are discussed in more detail below.

The present invention is directed to plants that exhibit a "constitutive SAR response." This term indicates that the SAR response is exhibited by a plant even in the absence of the conventional triggering event, i.e., pathogen invasion. However, the term does not require that the plant exhibit the SAR response at all times in development, simply that the response is exhibited without the need for the pathogen trigger.

N gene: A gene that encodes an N and an N-tr protein and which, when introduced into a plant such as tobacco, enhances the resistance of that plant to TMV infection. The prototypical N gene is the gene isolated from *N. glutinosa* and disclosed in U.S. Pat. No. 5,571,706. The sequence of this gene, including 5' and 3' regulatory regions, is shown in SEQ ID NO:1. The ability of an N gene to confer TMV resistance may readily be determined by scoring the HR and SAR responses to TMV infection in transgenic plants, and by monitoring systemic spread of the virus, as described below.

The disclosed N gene sequence is designated as the prototypical N gene since it is the first N gene to have been isolated. As discussed above, the present invention is not limited to use of prototypical R genes, but may be practiced using homologs and sequence variants. For example, U.S. Pat. No. 5,571,706, discusses how functional homologs of the N gene may be obtained from other plant species, such as from other Solanaceous species. Such homologs encode proteins having specified levels of sequence identity with the prototype N protein (e.g., at least 60% sequence identity), and retain N gene function, i.e., retain the ability to confer TMV resistance when introduced into plants. Similarly, the disclosed N and N-tr proteins are the prototypes of such proteins, and homologs of these proteins are encoded by N gene homologs. Accordingly, where reference is made herein to molecules relating to the N gene, for example, cDNA-N, N or N-tr proteins and introns of the N gene (such as I3), it will be understood that such reference includes not only the prototypical sequences of these molecules disclosed herein, but also corresponding sequences from N gene homologs. Also included within the scope of such terms are molecules that differ from the disclosed prototypical molecules by minor variations, such as nucleic acid molecules that vary from the disclosed sequences by virtue of the degeneracy of the genetic code, and nucleic acid sequences that have been modified to encode N or N-tr proteins having conservative amino acid substitutions. Such variant sequences may be produced by manipulating the nucleotide sequence of the tobacco cDNA-N or N gene using standard procedures such as site-directed mutagenesis or the polymerase chain reaction.

N tobacco: A tobacco line that carries at least one copy of an N gene. A plant that is homozygous for the N gene is designated NN, while a plant lacking a functional N gene is designated nn.

N protein/N-tr protein: Proteins encoded by an N gene. The N protein encoded by the prototypical N gene is shown in SEQ ID NO:3. The N-tr protein is a truncated form of the N protein and is encoded by an alternatively spliced form of the N gene; the prototypical sequence of N-tr is shown in SEQ ID NO:5. Expression of both forms of the protein in a plant cell is required for TMV resistance.

cDNA-N: A cDNA molecule that encodes an N protein. The nucleic acid sequence of the prototypical cDNA-N is shown in SEQ ID NO:2.

cDNA-N-tr: A cDNA molecule that encodes an N-tr protein. The nucleic acid sequence of the prototypical cDNA-N-tr is shown in SEQ ID NO:4.

pN/cDNA-N/intron 3/3'-GRS: While nn transgenic plants that contain an N-gene transgene show enhanced resistance to TMV infection, it has been shown that nn plants expressing cDNA-N or cDNA-N-tr transgene constructs do not. However, the expression of a construct comprising the N gene promoter (pN) operably linked to a form of cDNA-N that retains the third intron (I3) of the N gene, and in turn linked to the N gene 3' regulatory region (3'-GRS), does confer TMV resistance. Because intron 3 (I3) includes the alternatively spliced exon of the N gene (see Whitham et al., 1994), such constructs express both the N and N-tr proteins. Hence a construct of this arrangement (referred to as a pN/cDNA-N/intron 3/3'-GRS construct) may be used in this application in place of an N gene.

Sequence identity: The similarity between two nucleic acid sequences, or two amino acid sequences is expressed in terms of the similarity or identity between the sequences. Sequence identity is frequently measured in terms of percentage; the higher the percentage, the more alike the two sequences are. Homologs of prototype R proteins will possess a relatively high degree of sequence identity when aligned using standard methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx.

Homologs of prototype R proteins are typically characterized by possession of at least 50% sequence identity counted over the full-length alignment with the amino acid sequence of the selected prototype R protein using the NCBI Blast 2.0, gapped blastp set to default parameters. Proteins with even greater similarity to the reference sequences will show increasing percentage identities when assessed by this method, such as at least 60%, at least 70%, at least 75%, at least 80%, at least 90% or at least 95% sequence identity. When less than the entire sequence is being compared for sequence identity, homologs will typically possess at least 75% sequence identity over short windows of 10–20 amino acids, and may possess sequence identities of at least 85% or at least 90% or 95% depending on their similarity to the reference sequence. One of skill in the art will appreciate that these sequence identity ranges are provided for guidance only; it is entirely possible that strongly significant homologs could be obtained that fall outside of the ranges provided.

Oligonucleotide: A linear polynucleotide sequence of up to about 100 nucleotide bases in length.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Isolated: An "isolated" biological component (such as a nucleic acid or protein or organelle) has been substantially separated or purified away from other biological components in the cell of the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Purified: The term purified does not require absolute purity; rather, it is intended as a relative term. Thus, for example, a purified N protein preparation is one in which the N protein is more enriched than the protein is in its natural environment within a plant cell. Generally, a preparation of N protein is purified such that the N protein represents at least 5% of the total protein content of the preparation. For particular applications, higher purity may be desired, such that preparations in which the N protein represents at least 20% or at least 50% of the total protein content may be employed.

Ortholog: Two nucleotide or amino acid sequences are orthologs of each other if they share a common ancestral sequence and diverged when a species carrying that ancestral sequence split into two species. Orthologous sequences are also homologous sequences.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Alternatively, two protein coding sequences can be operably linked such that the sequences are placed in the same reading frame so as to produce a single open reading frame comprising the two protein coding sequences. Generally, operably linked DNA sequences are contiguous and, where necessary to join two protein-coding regions, in the same reading frame.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

cDNA (complementary DNA): A piece of DNA generally lacking internal, non-coding segments (introns) and regulatory sequences that determine transcription. cDNA is synthesized in the laboratory by reverse transcription from messenger RNA extracted from cells. It is recognized, however, that certain embodiments of the invention involve the use of nucleic acid constructs comprising cDNA sequences and the sequences of one or more introns, such as, for example, the pN/cDNA-N/intron 3/3'-GRS construct described, supra. Thus, the use herein of the term "cDNA" is not intended to exclude such constructs.

ORF (open reading frame): A series of nucleotide triplets (codons) coding for amino acids without any termination codons. These sequences are usually translatable into a peptide.

Transgenic plant: As used herein, this term refers to a plant that contains recombinant genetic material not normally found in plants of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually).

Transgene: As used herein, the term transgene refers to recombinant genetic material residing in cells of a plant.

III. Design of Genetic Constructs

The following sections and Examples provide detailed guidance on the design, and use of nucleic acid constructs for producing constitutive SAR plants. Standard molecular biology methods are used to practice the present invention, unless otherwise described. Such standard methods are described in Sambrook et al. (1989), Ausubel et al (1987) and Innis et al (1990).

Generally speaking, constitutive SAR plants produced according to the present invention comprise two genetic elements that together produce the SAR response. These elements are:

(1) an R gene or a cDNA encoding the R gene product(s); and (2) a transgene comprising a coding sequence for a product of the R gene or a portion thereof that is effective to produce the SAR response when co-expressed in the plant with element (1).

The first element may be a native R gene or a transgene, or a cDNA encoding the protein product(s) of the R gene (cDNA-R). Generally, this element will be expressed under the regulatory control of the native R gene promoter and 3' regulatory sequences, although other regulatory sequences known in the art may also be employed. Expression of this first genetic element in the plant will ordinarily confer enhanced resistance to one or more phytopathogens. Where the first element is a transgene, plant transformation methods (as described further in the following section) are used to introduce the transgene. It will be appreciated by one of skill in the art that where this element is a native R gene, transformation will be required only to introduce the second genetic element.

The second genetic element is a transgene that expresses either a product of the R gene (i.e., an R protein), or a portion thereof that is effective to produce the SAR response when co-expressed with the product of the first genetic element. This transgene may thus be an R gene, a cDNA derived from the R gene and encoding the R gene product(s) (i.e., cDNA-R), or another construct expressing an effective portion of the R protein. The term "effective portion" of the R protein refers to any part of the R protein that, when co-expressed in the plant with the product(s) of the first genetic element, produces an SAR response even in the absence of pathogen infection. By way of example, when the first genetic element is the tobacco N gene, the TIR domain of the N protein is an effective portion of the N protein. Thus, the second genetic element may be a genetic construct that expresses the TIR domain of the N protein.

One of skill in the art will appreciate that the determination of whether a particular portion of the R protein constitutes an "effective portion" may readily be determined using standard experimental procedures. Briefly, a plant carrying the selected R gene (the first genetic element) is transformed with a genetic construct encoding the region of the R protein to be tested. $T_0$ plants are selected, and assayed for the presence of the SAR response (in the absence of infecting pathogen) using standard techniques (such as detecting the expression of PR-1 proteins in the absence of pathogen infection) as described below. The presence of the SAR response indicates that the region of the R protein encoded by the genetic construct does constitute an effective portion of the R protein.

Typically, the second genetic element is designed such that the encoded protein is expressed under the control of regulatory regions or promoter known to produce high-level protein expression. Such regulatory regions may confer constitutive expression of the second genetic element, or may be inducible, such that the expression is turned on only in certain tissues, at defined developmental stages, or in response to application of an inducing agent. In general, the promoter of the second genetic element is a heterlogous promoter. Such a heterologous promoter is a promoter that is not native to the nucleotide sequence that is transcribed. In this instance, a heterologous promoter is any promoter that is not the native promoter of R gene which encodes the R protein, or portion thereof, of the second genetic element.

In particular embodiments, the R gene used, or from which the cDNA-R is derived, is an R gene having a TIR domain (see Table 1 for examples of R genes having a TIR domain). In this instance, the first genetic element may be the R gene, and the second genetic element may be a construct that expresses a protein or polypetide comprising the TIR domain, or an effective portion of the TIR domain.

In other particular embodiments, the second genetic element is a trangene that comprises a coding sequence for a polypeptide consisting essentially of a TIR domain, or an effective portion. By "polypeptide consisting essentially of a TIR domain, or an effective portion thereof" is intended a polypeptide consisting of: an amino acid sequence of a TIR domain or an effective portion thereof and optionally includes additional amino acids adjacent to the TIR domain or effective portion thereof. The additional amino acids can be adjacent to the N-terminal end and/or the C-terminal end of the TIR domain or effective portion thereof. While the additional amino acids can include those that are found adjacent to the TIR domain or effective portion thereof in a native R protein, the polypetide, in this instance, does not possess the amino acid sequence of the full-length, native R-protein. Furthermore, the presence of the additional amino acids in the polypeptide will not affect the capability of the polypeptide to produce a SAR response in the absence of an infecting pathogen, when co-expressed in a plant comprising the first and second genetic elements as described supra.

In yet other embodiments of the invention, the R gene selected is the tobacco N gene. Where the N gene is used as the basis for embodiments of the invention, it should be noted that introduction of either cDNA-N or cDNA-N-tr into TMV susceptible tobacco does not produce resistance to TMV infection. Thus, these forms of the cDNA are not generally useful as the first genetic element. However, introduction of a cDNA construct comprising pN/cDNA-N/intron 3/3'-GRS does produce TMV resistance. As described above, this construct includes the alternatively spliced exon, and thus encodes both of the N gene products-the N protein and the N-tr protein. Therefore, where the selected R gene is the tobacco N gene, the first genetic element may be, for example, the N gene, pN/cDNA-N/intron 3/3'-GRS, or another form of the N cDNA that includes the alternatively spliced exon and which, when expressed in TMV susceptible tobacco produces enhanced TMV resistance. The second genetic element may be, for example, cDNA-N, cDNA-N-tr, or a construct that expresses the N protein TIR domain, or an effective portion thereof.

The transgenic plants of the invention find use in methods for increasing the disease resistance of plants. Such plants display increased resistance to plant pathogens. The methods of the invention for increasing the disease resistance of plants involve plants having a first and second genetic element or nucleic acid molecule as described supra. The methods comprise obtaining a plant having a first nucleic acid molecule encoding one or more protein products of an R gene sufficient to confer resistance to a phytopathogen; and then introducing into the genome of said plant a second nucleic acid molecule comprising at least one polypeptide encoded by the R gene, wherein co-expression of the first and second nucleic acid molecules is sufficient to produce a systemic acquired resistance response in the plant. The R gene of the first nucleic acid molecule can be native to the plant. That is the R gene occurs as part of a native nucleic acid molecule of the plant, such as, for example, a nucleic acid molecule of a chromosome. Alternatively, if the plant lacks a desired R gene, the methods of the invention additionally involve introducing into the genome of the plant a first nucleic acid molecule comprising the desired R gene.

IV. Plant Transformation

Plant transformation techniques are now routinely performed and are well known in the art. The nucleic acid molecules, transgenes, or genetic elements of the invention can be introduced into the genome of a plant using plant transformation methods known in the art. As discussed above, the second genetic element is typically a transgene and so is introduced into the plant species in question using such techniques. The first genetic element may be a native gene or a transgene.

Where the first genetic element is a transgene, it too is introduced into the plant species by transformation. When the first genetic element is introduced by transformation, it may be co-transformed with the second genetic element, or each element may be separately transformed, such that plant lines separately carrying each of the elements are produced. The elements may then be brought together by conventional plant breeding techniques.

Where the first genetic element is a native gene, the second genetic element may be introduced into a plant carrying the first genetic element. Alternatively, the second genetic element may be transformed into a plant of the same species, and the two elements may be brought together by crossing plants carrying the (native) first genetic element and the second (transgenic) element.

Constructs to be transformed into the plant lines are typically cloned into a suitable transformation vector, which is then introduced into plant cells by one of a number of techniques (e.g., electroporation). Progeny plants are regenerated from the transformed plant material, and those progeny plants containing the introduced construct are selected.

Selection of progeny plants containing the introduced transgene may be made based upon the detection of an altered phenotype. Such a phenotype may result directly from the introduced transgene (e.g., a constitutive SAR response) or may be manifested as enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include, but are not limited to, U.S. Pat. No. 5,571,706 ("Plant Virus Resistance Gene and Methods"); U.S. Pat. No 5,677,175 ("Plant Pathogen Induced Proteins"); U.S. Pat. No. 5,510,471 ("Chimeric Gene for the Transformation of Plants"); U.S. Pat. No. 5,750,386 ("Pathogen-Resistant Transgenic Plants"); U.S. Pat. No. 5,597,945 ("Plants Genetically Enhanced for Disease Resistance"); U.S. Pat. No. 5,589,615 ("Process for the Production of Transgenic Plants with Increased Nutritional Value Via the Expression of Modified 2S Storage Albumins"); U.S. Pat. No. 5,750,871 ("Transformation and Foreign Gene Expression in Brassica Species"); U.S. Pat. No. 5,268,526 ("Overexpression of Phytochrome in Transgenic Plants").

These examples include descriptions of transformation vector selection, transformation techniques and the construction of constructs designed to over-express an introduced transgene. In light of the foregoing and the teaching herein of genetic constructs designed to produce a constitutive SAR response, one of skill in the art will be able to introduce these constructs into plants in order to produce plants having a constitutive SAR response and therefore enhanced broad-spectrum disease resistance.

a. Plant Types

Because all plant types are susceptible to one or more plant pathogens, the present invention may be usefully applied to produce broad-spectrum resistance in any plant type. Thus, the invention may be applied to both monocotyledonous and dicotyledenous plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, Brassica, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchides, carnations and roses.

By way of example, TMV is a serious pathogen of Solanaceous species such as tobacco (Nicotiana sp.), tomato (Lycopersicon sp.) and pepper (Capsicum sp.) and is able to infect potato (Solanum sp.). Thus, the use of N gene-based constructs as described herein to produce constitutive SAR plants of these species will be particularly valuable to provide enhanced resistance against not only TMV, but also a broad range of other viruses and bacteria and fungal pathogens that infect these species.

b. Vector Construction

A number of recombinant vectors suitable for stable transfection of plant cells or for the establishment of transgenic plants have been described including those described in Weissbach and Weissbach, (1989), and Gelvin et al., (1990). Typically, plant transformation vectors include one or more cloned plant genes (or cDNAs) under the transcriptional control of 5' and 3' regulatory sequences, together with a dominant selectable marker. Such plant transformation vectors typically also contain a promoter regulatory region (e.g., a regulatory region controlling inducible or constitutive, environmentally or developmentally regulated, or cell- or tissue-specific expression), a transcription initiation start site, a ribosome binding site, an RNA processing signal, a transcription termination site, and/or a polyadenylation signal. As described above, the first genetic element according to the present invention may be a native R gene, in which case the gene is already present in the plant genome to be transformed. In cases where the first genetic element is a heterologous R gene, it may be introduced into the plant tissue using a transformation vector, but will typically be used with its own regulatory sequences.

The second genetic element is generally constructed using regulatory sequences that produce expression levels that are higher than expression levels produced by the regulatory sequences of the corresponding R gene. Such regulatory sequences may provide constitutive expression (i.e., expression regardless of triggering stimulus) or expression that is inducible (i.e., expression in response to a triggering stimulus) or expression that is tissue-specific (i.e., expression that is restricted to, or enhanced in, certain tissues of the plant).

Examples of constitutive plant promoters that may be useful for expressing the second genetic element include: the cauliflower mosaic virus (CaMV) 35S promoter, which confers constitutive, high-level expression in most plant tissues (see, e.g., Odel et al., 1985, Dekeyser et al., 1990, Terada and Shimamoto, 1990; Benfey and Chua, 1990); the nopaline synthase promoter (An et al., 1988); and the octopine synthase promoter (Fromm et al., 1989).

A variety of plant gene promoters that are regulated in response to environmental, hormonal, chemical, and/or developmental signals, also can be used for expression of the cDNA in plant cells, including promoters regulated by (a) heat (Callis et al, 1988; Ainley, et al. 1993; Gilmartin et al. 1992); (b) light (e.g., the pea rbcS-3A promoter, Kuhlemeier et al., 1989, and the maize rbcS promoter, Schaffner and Sheen, 1991); (c) hormones and other signaling molecules, such as abscisic acid (Marcotte et al., 1989), methyl jasmonate or salicylic acid (see also Gatz et al., 1997); and (d) wounding (e.g., wunI, Siebertz et al., 1989).

Chemical-regulated promoters can be used to modulate the expression of a nucleic acid construct of the invention in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814, 618 and 5,789,156), herein incorporated by reference.

Alternatively, tissue specific (root, leaf, flower, and seed for example) promoters (Carpenter et al. 1992, Denis et al. 1993, Opperman et al. 1993, Yamamoto et al. (1991) *Plant Cell* 3:371–82, Stockhause et al. 1997; Roshal et al., 1987; Schernthaner et al., 1988; and Bustos et al., 1989) can be fused to the coding sequence to obtained particular expression in respective organs.

Plant transformation vectors may also include RNA processing signals, for example, introns, which may be positioned upstream or downstream of the ORF sequence in the transgene. In addition, the expression vectors may also include additional regulatory sequences from the 3'-untranslated region of plant genes, e.g., a 3' terminator region to increase mRNA stability of the mRNA, such as the PI-II terminator region of potato or the octopine or nopaline synthase (NOS) 3' terminator regions.

Finally, as noted above, plant transformation vectors may also include dominant selectable marker genes to allow for the ready selection of transformants. Such genes include those encoding antibiotic resistance genes (e.g., resistance to hygromycin, kanamycin, bleomycin, G418, streptomycin or spectinomycin) and herbicide resistance genes (e.g., phosphinothricin acetyltransferase).

c. Transformation and Regeneration Techniques

Transformation and regeneration of both monocotyledonous and dicotyledonous plant cells is now routine, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG) mediated transformation; transformation using viruses; microinjection of plant cells; micro-projectile bombardment of plant cells; vacuum infiltration; and *Agrobacterium tumefaciens* (AT) mediated transformation. Typical procedures for transforming and regenerating plants are described in the patent documents listed at the beginning of this section.

d. Selection of Transformed Plants

Following transformation and regeneration of plants with the transformation vector, transformed plants are usually selected using a dominant selectable marker incorporated into the transformation vector. Typically, such a marker will confer antibiotic resistance on the seedlings of transformed plants, and selection of transformants can be accomplished by exposing the seedlings to appropriate concentrations of the antibiotic.

After transformed plants are selected and grown to maturity, they can be assayed using the methods described below to assess whether a constitutive SAR phenotype is expressed.

V. Assessment of Systemic Acquired Resistance (SAR) Response

The SAR response can be distinguished from other disease resistance responses both functionally and at the molecular level. Functionally, the SAR provides enhanced resistance against a broad spectrum of pathogens. At the molecular level, the SAR response is associated with the expression of a number of SAR-specific proteins.

SAR proteins are proteins that are closely associated with the maintenance of a resistance response; many of these proteins belong to the class of pathogenesis-related (PR) proteins. PR proteins were originally identified in tobacco as novel proteins that accumulate after TMV infection (Ryals et al., 1996). In tobacco, SAR proteins fall into about nine families: acidic forms of PR-1 (PR-1a, PR-1b and PR-1c); beta-1,3-glucanase (PR-2a, PR-2b and PR-2c); class II chitinases (PR-3a and PR-3b, also termed PR-Q); hevein-like protein (PR-4a and PR-4b); thaumatin-like protein (PR-5a and PR-5b); acidic and basic isoforms class III chitinase; an extracellular beta-1,3-glucanase (PR-Q'); and the basic isoform of PR-1 (Ward et al., 1991). In Arabidopsis, the SAR marker proteins are PR-1, PR-2 and PR-5 (Uknes et al., 1992). The genes encoding these SAR markers have been cloned and characterized and used extensively to evaluate the onset of SAR (see Ward et al., 1991, and Uknes et al., 1992). The relative expression of the various SAR proteins vary between species. For example, acidic PR-1 is weakly expressed in the SAR response in cucumber, but is the predominant SAR protein in tobacco and Arabidopsis. Conserved homologs of SAR proteins, including PR-1, have been identified in monocotyledenous species, including maize and barley.

The PR-1 proteins are highly conserved and so represent a good molecular marker for detecting SAR. A constitutive SAR response may thus be detected by growing plants in the absence of pathogen, and then assaying for the expression of PR-1 RNA or protein. Plants carrying the R gene that are either exposed or not exposed to the pathogen may be used as positive and negative controls, respectively. Because PR-1 proteins are highly conserved, antibodies that raised against the tobacco PR-1 proteins, including the PR-1c protein, also recognize PR-1 proteins from other plant species (see Takahashi et al., 1994). Therefore, anti-PR-1 antibodies may conveniently be used across a range of plant species to detect SAR proteins.

At the functional level, the SAR response provides enhanced resistance to a wide range of pathogens. While the individual assays for detecting such resistance will vary depending on the particular pathogen, the general observation of enhanced resistance against a number of pathogens (compared to a control R plant) in the absence of a prior triggering infection is indicative of a constitutive SAR response.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. While the invention does not depend of any particular reduction in the severity of disease symptoms, the methods and plants of the invention will generally reduce the disease symptoms resulting from a pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

The transgenic plants of the invention display enhanced resistance to plant pathogens or phytopathogens, including but are not limited to, viruses or viroids, bacteria, insects, nematodes, fungi, and the like. Viruses include any plant virus, for example, TMV, tobacco or cucumber mosaic virus, ringspot virus, necrosis virus, maize dwarf mosaic virus, etc. Specific fungal and viral pathogens for the major crops include: Soybeans: *Phytophthora megasperma* fsp. glycinea, *Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassuicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata, Soybean mosaic* virus, *Glomerella glycines*, Tobacco Ring spot virus, Tobacco Streak virus, *Phakopsora pachyrhizi, Pythium aphanidermatum, Pythium ultimum,*

*Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassicola, Pythium ultimum, Peronospora parasitica, Fusarium roseum, Alternaria alternata;* Alfalfa: *Clavibater michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium, Xanthomonas campestris* p.v. *alfalfae, Aphanomyces euteiches, Stemphylium herbarum, Stemphylium alfalfae*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana,* Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmophora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis;* Corn: *Fusarium moniliforme* var. *subglutinans, Erwinia stewartii, Fusarium moniliforme, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillusflavus, Bipolaris maydis O, T (Cochliobolus heterostrophus), Helminthosporium carbonum I, II & III (Cochliobolus carbonum), Exserohilum turcicum I, II & III, Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvulariapallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. zea, *Erwinia carotovora, Corn stunt spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium,* Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, Colletotrichum graminicola* (*Glomerella graminicola*), *Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Pseudomonas avenae* (*Pseudomonas alboprecipitans*), *Ramulispora sorghi, Ramulispora sorghicola, Phyllachara sacchari, Sporisorium reilianum* (*Sphacelotheca reiliana*), *Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, and lesion nematodes, including Heterodera and Globodera spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

VI. Obtaining R Gene Homologs and Sequence Variants

The Examples provided below utilized the prototypical tobacco N gene and related cDNA molecules as described by Whitham et al. (1994). However, as described above, the invention is not limited to the use of prototypical R genes, but may be practiced using R gene homologs and sequence variants that differ in exact sequence from the prototype sequences.

R Gene Homologs

R gene homologs may be obtained from closely or distantly related plant species by conventional molecular biology methods, including polymerase chain reaction-based techniques and nucleic acid hybridization.

By way of example, homologs of the N gene are present in a number of plant species including tomato and other varieties of tobacco. Such homologs may also be used to produce constitutive SAR plants as described herein. As described above, homologs of the disclosed N gene confer TMV resistance when introduced into otherwise susceptible plants and encode N and N-tr that are typically characterized by possession of at least 50% sequence identity counted over the full-length alignment with the amino acid sequence of the prototype N and N-tr sequences using the NCBI Blast 2.0, gapped blastp set to default parameters. Proteins with even greater similarity to the reference sequences will show increasing percentage identities when assessed by this method, such as at least about 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the reference sequence.

Both conventional hybridization and PCR amplification procedures may be utilized to clone sequences encoding N and N-tr homologs. Common to both of these techniques is the hybridization of probes or primers derived from the prototype cDNA-N or N gene sequence to a target nucleotide preparation, which may be, in the case of conventional hybridization approaches, a cDNA or genomic library or, in the case of PCR amplification, a cDNA or genomic library, or an mRNA preparation. Amplification of, or hybridization to, a cDNA library in order to obtain N homologs should preferably be performed on a cDNA library made from a plant infected with TMV so that the N homolog is actively expressed in the cells from which the library is made.

Direct PCR amplification may be performed on cDNA or genomic libraries prepared from the plant species in question, or RT-PCR may be performed using mRNA extracted from the plant cells using standard methods. PCR primers will typically, but not necessarily, comprise at least about 10 consecutive nucleotides of the tobacco cDNA-N or N gene. One of skill in the art will appreciate that sequence differences between the tobacco cDNA-N or N gene and the target nucleic acid to be amplified may result in lower amplification efficiencies. To compensate for this, longer PCR primers or lower annealing temperatures may be used during the amplification cycle. Where lower annealing temperatures are used, sequential rounds of amplification using nested primer pairs may be necessary to enhance specificity.

Degenerate PCR primers, which are well known to those of ordinary skill in the art, can also be employed for PCR amplification. A degenerate primers is not a primer consisting of a single nucleotide sequence, but rather is a mixture of primers of different nucleotide sequences which are capable of encoding for an amino acid sequence that corresponds to a particular portion of the coding sequence of a gene interest. Because of the degeneracy of the genetic code, a particular amino acid can be specified by more than one codon. A degenerate primers is thus synthesized to take in to account the degeneracy of the genetic code and will typically include all possible nucleotide sequences that could encode the amino acid sequence of that portion of the protein to which the primer corresponds. In producing such degenerate primers, it is recognized that not all organisms use all possible codons to specify a particular amino acid, and some organisms, and some particular genomes in an organism, such as, for example, the mitochondrial genome, do not follow the universal genetic code. Accordingly, it will typically be preferable to synthesize a degenerate oligonucleotide primer based on the genetic code and codon usage in an organism or within a particular genome of an organism. Such genetic codes, codon usage, and methods for their determination are known in the art.

For conventional hybridization techniques the hybridization probe is preferably conjugated with a detectable label such as a radioactive label, and the probe is preferably of at least 20 nucleotides in length. As is well known in the art, increasing the length of hybridization probes tends to give enhanced specificity. The labeled probe derived from the tobacco cDNA-N or N gene sequence may be hybridized to a plant cDNA or genomic library and the hybridization signal detected using means known in the art. The hybridizing colony or plaque (depending on the type of library used) is then purified and the cloned sequence contained in that colony or plaque isolated and characterized.

Homologs of the tobacco cDNA-N or N gene may alternatively be obtained by immunoscreening of an expression library. With the provision of the disclosed N gene and encoded proteins, the N or N-tr proteins may be expressed and purified in a heterologous expression system (e.g., *E. coli*) and used to raise antibodies (monoclonal or polyclonal) specific for the N or N-tr protein. Antibodies may also be raised against synthetic peptides derived from the tobacco N or N-tr amino acid sequences. Methods of raising antibodies are well known in the art and are described in Harlow and Lane (1988). Such antibodies can then be used to screen an expression cDNA library produced from the plant from which it is desired to clone the N homolog using routine methods. The selected cDNAs can be confirmed by sequencing and enzyme activity.

Parallel approaches may be employed to obtain homologs of other R genes, such as Prf and L6.

Variant Sequences

Variant R proteins include proteins that differ in amino acid sequence from the selected prototypical R protein sequence. Such proteins may be produced by manipulating the nucleotide sequence of the prototype cDNA-R or R gene using standard procedures such as site-directed mutagenesis or the polymerase chain reaction. The simplest modifications involve the substitution of one or more amino acids for amino acids having similar biochemical properties. These so-called conservative substitutions are likely to have minimal impact on the activity of the resultant protein. Table 3 shows amino acids that may be substituted for an original amino acid in a protein and which are regarded as conservative substitutions.

TABLE 3

| Original Residue | Conservative Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | tip; phe |
| Val | ile; leu |

More substantial changes in biological function or other features may be obtained by selecting substitutions that are less conservative than those in Table 3, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine. The effects of these amino acid substitutions or deletions or additions may be assessed for R protein derivatives by analyzing the ability of a nucleic acid molecule encoding the derivative proteins to produce a constitutive SAR response when used in conjunction with the techings of this invention.

Variant R cDNAs or R genes may be produced by standard DNA mutagenesis techniques, for example, M13 primer mutagenesis. Details of these techniques are provided in Sambrook et al. (1989), Ch. 15. By the use of such techniques, variants may be created which differ in minor ways from the prototypical R gene nucleic acid sequences, yet which still retain R gene function. In their simplest form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence in such a way that, while the nucleotide sequence is substantially altered, it nevertheless encodes proteins having amino acid sequences identical or substantially identical to the prototype R protein sequences. For example, the second amino acid residue of the prototype N protein is alanine. This is encoded in the prototype N gene open reading frame (ORF) by the nucleotide codon triplet GCA. Because of the degeneracy of the genetic code, three other nucleotide codon triplets—GCT, GCC and GCG—also code for alanine. Thus, the nucleotide sequence of the N ORF could be changed at this position to any of these three codons without affecting, the amino acid composition of the encoded protein or the characteristics of the protein. Based upon the degeneracy of the genetic code, variant DNA molecules may be derived from R cDNA and gene sequences using standard DNA mutagenesis techniques as described above, or by synthesis of DNA sequences.

The following Examples are offered by way of illustration and not by way of limitation.

EXAMPLES

Example 1

Overexpression of N cDNAs in NN Tobacco Plants Induces a Constitutive Systemic Acquired Resistance Phenotype, even in the Absence of TMV Infection A. Vector Construction and Plant Transformation cDNA-N and cDNA-N-tr were cloned into the T-DNA vector pOCA28 (Olszewski et al., 1988; gift from F. Ausubel, Harvard Medical School). These constructs place cDNA expression under the regulatory control of the 35S promoter and the NOS terminator. The resulting vectors were transformed into TMV resistant tobacco (Samsun::NN) or TMV susceptible tobacco (SR1::nn) by Agrobacterium-mediated transformation (Horsch et al., 1985).

B. Expression of SAR Response

The lower leaves of $T_0$ transformants were inoculated with TMV (U1 strain) approximately 4 weeks after transfer to soil as described by Takahashi (1956) and Klement (1990). Following such inoculation, resistance or susceptibility of a plant to TMV and virus spread was assessed using standard assays, including determining HR and SAR responses, and detecting the presence of TMV in the upper leaves of the plant. The plants were also analyzed at approximately 10 weeks after transfer to soil.

With respect to HR, the inoculated leaves of a resistant tobacco plant show localized regions of necrosis around the site of TMV infection within about 48 hours after inoculation; the lesions are generally about 0.1 cm in diameter and TMV is restricted to the region immediately surrounding the necrotic lesions. In contrast, leaves of susceptible plants generally show no lesions, the TMV spreads systemically, and the leaves develop mosaic symptoms characterized by intermittent areas of light and dark leaf tissue.

The SAR response was determined functionally about 7–10 days after inoculation of the lower leaves, by inoculating upper leaves of the plant in the same manner. A TMV resistant plant in which the SAR has been triggered by the earlier inoculation will show HR lesions on these upper leaves within about 48 hours of the second inoculation, but the lesions are typically fewer and significantly smaller (0.03–0.05 cm diameter) than the HR lesions on the lower leaves. A susceptible plant will again show no lesions, and the mosaic patterning signifying systemic infection will be observed on the upper leaves.

The SAR response was detected at the molecular level by detecting PR-1a RNA using a standard Northern Blot procedure. Total RNA was extracted from upper leaves of 4- or 10-week-old plants. Certain of the plants were first inoculated with TMV on their lower leaves, and the upper leaves were harvested approximately 10 days after inoculation. Following electrophoresis and Northern blotting of the RNA, the filters were hybridized with a probe comprising the tobacco PR-1a cDNA (Cornelissen et al., 1987).

Systemic spread of the virus can be detected in a number of ways. By visual inspection of the leaves, systemic infection can be detected by the appearance of the mosaic light and dark patches on the leaves away from the site of the initial inoculation. The presence of systemically spread virus can also be detected by a bioassay in which leaves of the inoculated test plant (taken from a part of the test plant distal from the initial inoculation ("distal leaves")) are rubbed onto an indicator plant (e.g., N. tabacum Samsun NN). The development of an HR response on the indicator plant indicates the presence of systemic spread of the virus through the test plant. Additionally, systemic spread of the virus may be detected at the molecular level by removing distal leaves, extracting RNA using standard procedures and performing a Northern blot using a radiolabeled probe derived from the TMV genome. In this test, systemic spread is indicated by the presence of TMV-hybridizing bands on the Northern blot. Alternatively, systemic spread of the virus may be detected immunologically, for example by ELISA of protein extracted from distal leaves using an anti-TMV protein antibody.

TMV infection of 4-week-old cDNA-N::Samsun NN or cDNA-N-tr::Samsun NN transgenic plants was observed to induce an HR similar to that induced by TMV in wild type N plants. However, the HR continued to spread throughout the plant resulting in death of the plant within about 10 days. The induced HR and subsequent plant death was not associated with virus spread. Thus, it appears that cDNA-N::Samsun NN or cDNA-N-tr::Samsun NN overexpressing transgenic plants when challenged with pathogen show a hyperactive response. One possible explanation for this is that a diffusible systemic signal generated in the inoculated leaf may act as a signal to induce death in the TMV uninfected parts of the plant. Notably, several virus types other than TMV (including tobacco rattle virus and tobacco etch virus) did not trigger this early phenotype.

Surprisingly, at about 10 weeks of soil growth (about the time of flowering) transgenic AN plants overexpressing cDNA-N or cDNA-N-tr showed a constitutive lesion phenotype without TMV infection (this phenotype is referred to as "lesion mimic"). The lesions started at leaf tips, and spread throughout the leaf within about 5 days. Lesions appeared only in the lower half of the plant. Overexpressing transgenic plants showing these constitutive lesions displayed an increased resistance or immunity when challenged with TMV pathogen. In addition, these plants show increased expression of pathogen related protein 1a (PR1a)

RNA, a well-characterized molecular marker of systemic acquired resistance (FIG. 2). Interestingly, PR-1a RNA levels appeared to be higher in overexpressing plants than in NN plants that had been triggered to produce SAR by prior inoculation with TMV (see FIG. 2).

The early (4 week) phenotype exhibited by the cDNA-N::Samsun NN and cDNA-N-tr::Samsun NN plants could be detrimental to crop plants grown in the field, since exposure to the triggering pathogen at this stage of development might be lethal. A number of approaches might be used to prevent this phenomenon. For example, since the early phenotype is apparently triggered only by the pathogen that corresponds to the particular R gene utilized, problems associated with the early phenotype could be minimized by selecting an R gene that confers resistance to a pathogen that does not typically cause significant disease in the plant type that is to be transformed (or in the geographic area in which the plant is to be grown). Alternatively, exposure of the plants to the triggering pathogen during early growth could be minimized by physical isolation (such as greenhouse growth). At the molecular level, the early phenotype may be avoided altogether by placing the expression of the second genetic element under the control of either an inducible promoter, or a promoter that is developmentally controlled. Thus, in the case of an inducible promoter, the inducing agent could be applied to the plants to turn on the SAR response later in development (for example, around 10 weeks). The use of an inducible promoter is also advantageous in that the SAR response need not be turned if there is no pathogen problem in the crop. In the case of a developmentally controlled promoter, the promoter used would preferably cause expression of the second genetic element only after the plants had reached a maturity level where the early phenotype no longer occurs (around 10 weeks of age).

Example 2

Overexpression of the N TIR Domain in NN Plants Induces a Constitutive Systemic Acquired Resistance Phenotype, even in the Absence of TMV Infection To determine whether the entire N protein is required for this molecular-genetic activation of the SAR response, constructs were produced in which each of the three domains of the N protein—TIR, NBS and LRR—was independently expressed under the control of the 35S promoter and the NOS terminator. The constructs expressed the following sections of the N protein:

construct 1: amino acids 1–150 (including the TIR domain);
construct 2: amino acids 201–441 (including the NBS domain);
construct 3: amino acids 590–928 (including the LRR domain).

The constructs were transformed into Samsun::NN tobacco as described above, and the resulting transgenic plants were tested for SAR response in the absence of TMV infection, as well as following TMV infection.

TMV infection of 4-week-old NBS:Samsun NN and LRR:Samsun NN plants (i.e., Samsun NN plants transformed with the NBS and LRR domain constructs, respectively) produced the same response as TMV infection of 4-week-old untransformed Samsun NN plants, i.e., HR that contains the virus and prevents systemic spread. However, TMV infection of 4-week-old TIR:Samsun NN plants produced the same response as observed with cDNA-N::Samsun NN or cDNA-N-tr::Samsun NN plants, i.e., HR response followed by spread of the HR response (without corresponding systemic spread of the virus) and subsequent plant death.

Furthermore, at 10 weeks of age, and in the absence of TMV challenge, the TIR:Samsun NN plants also showed the constitutive SAR response seen with cDNA-N::Samsun NN or cDNA-N-tr::Samsun NN plants.

Example 3

Overexpression of the N-TIR Domain Induces a Constitutive HR Phenotype in the Absence of TMV Infection and Provides Resistance to Other Virulent Viral Pathogens Different regions of N-cDNA were expressed to further define the region of N-cDNA that is sufficient to the initiate constitutive defense response (HR and SAR) in the absence of TMV. TIR, NBS, and LRR regions of N-cDNA were independently inserted between the 35S promoter and NOS terminator in a pMB4 T-DNA vector. These constructs were transformed into SR1 nn (TMV susceptible) and Samsun NN (TMV resistant, wild-type N gene) tobacco plants by Agrobacterium-mediated transformation (Horsch et al., 1985). Transgenic TIR::Samsun NN plants overexpressing the TIR domain showed constitutive HR after 8–10 weeks in the absence of TMV infection (FIG. 3). However, overexpression of the NBS or LRR region of the N gene failed to induce this response (data not shown). This suggests that the 450 bp N-TIR region is sufficient to induce constitutive defense response when overexpressed in the background of the N gene. Furthermore, this phenotype is similar to that of the phenotype induced when N-cDNA or N-tr-cDNA is overexpressed in the wild-type N gene background.

Figure 4:
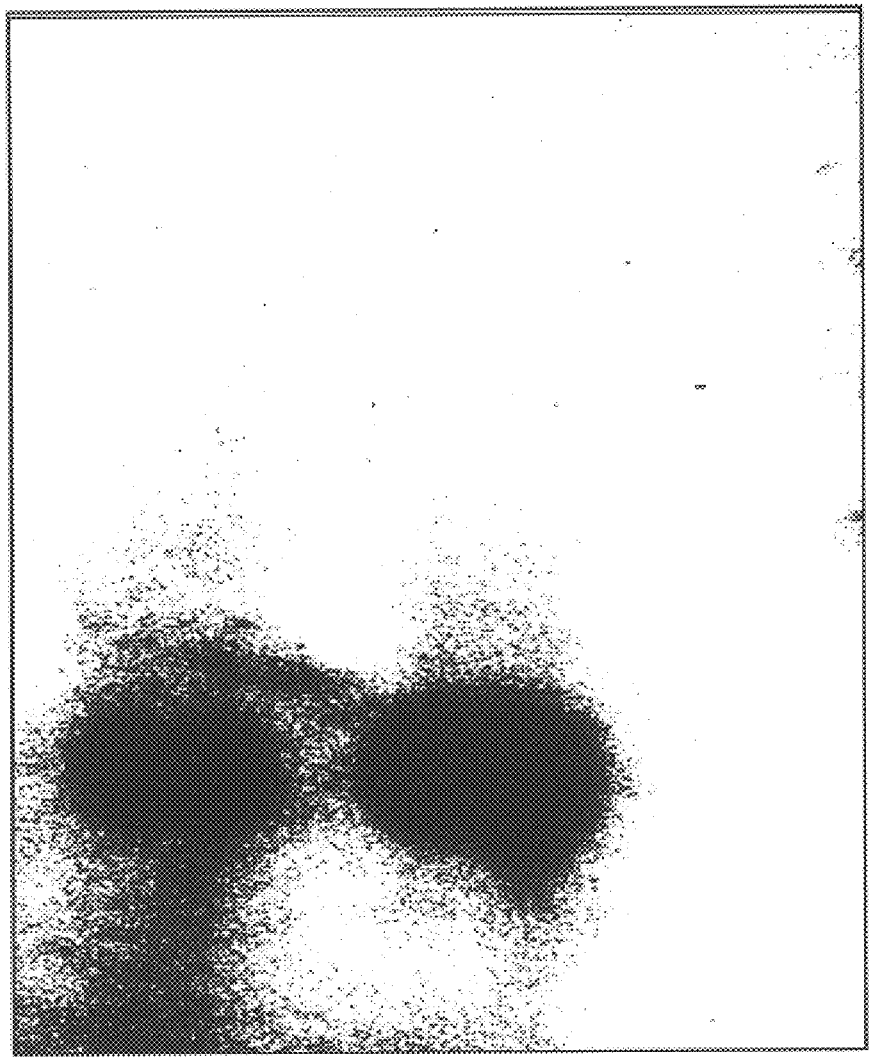
FIG. 4 shows a Northern analysis of TIR expression in TIR::Samsun NN transgenic plants and wild-type N gene containing Samsun NN plants.

To assess 35S-TIR expression in these plants, Northern analysis was performed using one $\mu$g poly (A)$^+$ RNA isolated from Samsun NN wild-type plants and two different TIR overexpressing 10- to 12-week-old sibling plants (FIG. 4, lanes 1 and 2). Wild-type N message in the Northern analysis was not detected, as it is expressed at a very low level. However, the wild-type N message was detected using RT-PCR (data not shown). These results indicate that the TIR message is overexpressed compared to the wild-type N gene containing Samsun NN plants (FIG. 4). Ongoing experiments will determine if the message expression correlates with TIR protein expression.

Figure 5:
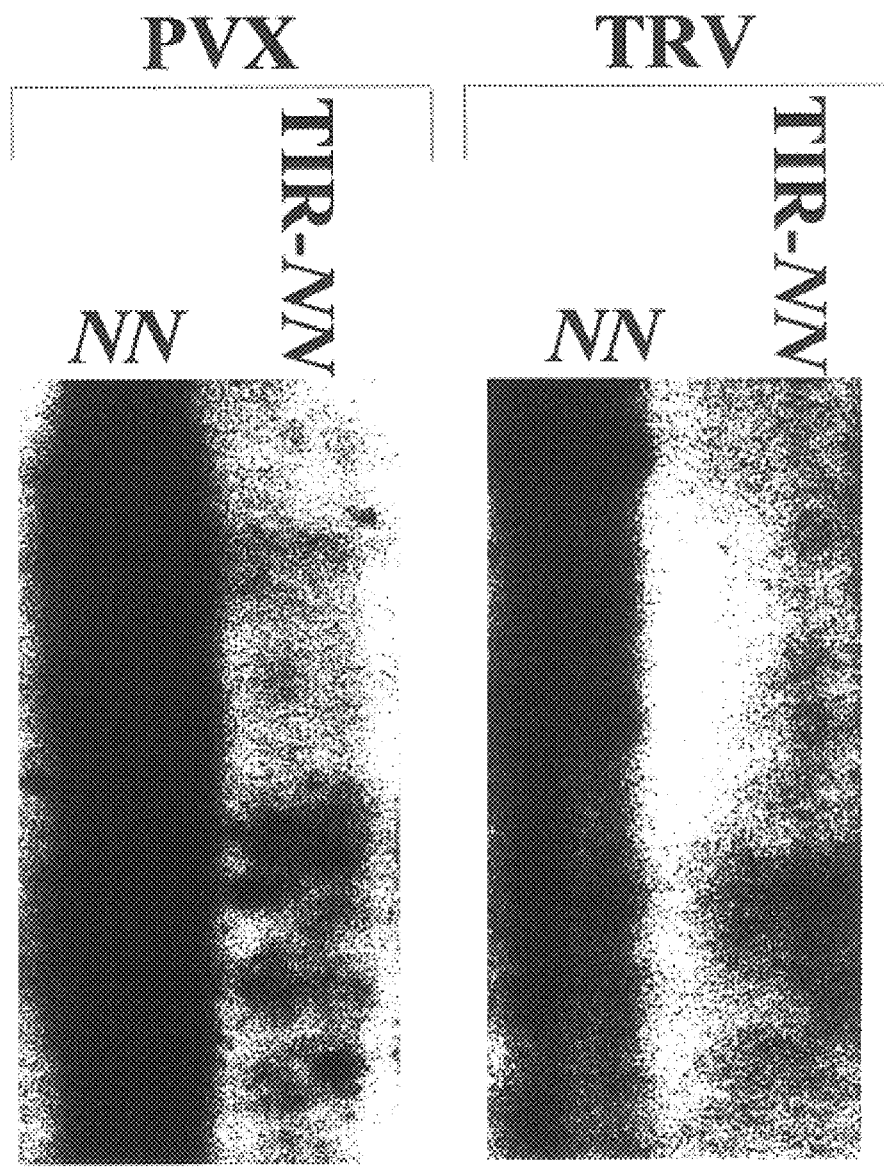
FIG. 5 compares replication of potato virus (PVX) and tobacco rattle virus (TRV) in TIR::Samsun NN transgenic plants and wild-type N gene containing Samsun NN plants.

Whether the constitutive HR induced by TIR overexpression induces resistance to other virulent viral pathogens, such as tobacco rattle virus (TRV, strain Ppk20), potato virus X (PVX), and tobacco etch virus (TEV), was examined. TIR::Samsun NN transgenic plants (10 to 12 weeks old) overexpressing TIR and exhibiting the constitutive HR phenotype and the wild-type Samsun NN plants were infected with known amounts of TRV, PVX, and TEV on leaves younger than those displaying HR. Two weeks after virus infection, RNA was extracted from the inoculated leaves. About 5 $\mu$g of total RNA was used in the Northern analysis. PVX virus replication was detected by Northern hybridization analysis using the PVX coat protein as a probe. The TRV probe consisted of approximately 500 bps of the 5' terminus of RNA1. Replication of TRV and PVX were reduced approximately 70–80% in the TIR::Samsun NN transgenic plants when compared to replication in the control Samsun NN plants (FIG. 5). These data suggest that TIR overexpressing plants resist replication of these viruses through TIR/N induced SAR.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Those skilled in the art will recognize, or be able to ascertain using no more than routine experimentation, many equivalents to the specific embodiments of the invention described herein. Such equivalents are intended to be encompassed by the following claims.

References

Agrios (1997) Plant Pathology, Academic Press (London).
Ainley et al. (1993) Plant Mol. Biol. 22:13–23.
Altschul & Gish (1996) Methods Enzymol., 266, 460–80.
Altschul et al. (1990) J Mol. Biol., 215, 403–10
Altschul et al. (1994) Nature Genet., 6, 119–29.
An et al. (1988) Plant Physiol. 88:547.
Anderson et al. (1997) Plant Cell 9: 641–651.
Ausubel et al. (1987) In Current Protocols in Molecular Biology, Greene Publishing Associates and Wiley-Intersciences.
Baker et al. (1997) Science 276:726–733.
Benfey & Chua (1990) Science 250:959–966.
Bent et al. (1994) Science 265:1856.
Botella et al (1998) Plant Cell 10:1857–1860.
Bustos et al. (1989) Plant Cell 1:839.
Cal et al. (1997) Science 275:832.
Callis et al. (1988) Plant Physiol. 88:965.
Cao et al. (1998) Proc. Natl. Acad. Sci. USA 95:6531–6536.
Caputi et al. (1994) Nuc. Acids. Res. 22:1018–1022.
Carpenter et al. (1992) The Plant Cell 4:557–571.
Cornelissen et al (1987) Nuc. Acids. Res. 15:6799–6811.
Corpet et al. (1988) Nucleic Acids Research 16, 10881–90.
Dekeyser et al. (1990) Plant Cell 2:591.
Denis et al. (1993) Plant Physiol. 101: 1295–1304.
Dixon et al. (1998) Plant Cell 10 (11): 1915–26.
Fromm et al. (1989) Plant Cell 1:977.
Gatz et al. (1997) Ann. Rev. Plant Physiol. Plant Mol. Biol. 48:89–108.
Gelvin et al. (1990) Plant Molecular Biology Manual, Kluwer Academic Publishers.
Gilmartin et al. (1992) The Plant Cell 4:839–949.
Grant et al. (1995) Science 269:843.
Hammond-Kosack and Jones (1996) Plant Cell 8 (10):1773–91.
Hammond-Kosack and Jones (1997) Ann. Rev. Plant. Physiol. Plant Mol. Biol. 48:575–607.
Hammond-Kosack et al. (1998) Plant Cell 10 (8) 1251–66.
Harlow & Lane (1988) Antibodies, A Laboratory Manual, Cold Spring Harbor
Higgins and Sharp (1988) Gene, 73:237–244.
Higgins and Sharp (1989). CABIOS 5:151–153.
Holmes (1946) Phytopathology 86:643–659.
Horsch et al. (1985) Science 227:1229–1231.
Huang, et al. (1992) Computer Applications in the Biosciences 8, 155–65.
Innis et al. (eds.) (1990) PCR Protocols, A Guide to Methods and Applications, Academic Press, Inc., San Diego, Calif.
Johal and Briggs (1992) Science 258:985.
Jones et al. (1994) Science 266:789.
Klement (1990) In Methods in Phytobacteriology (Klement et al., eds.) Akademiai Kiado (Budapest, Hungary).
Kuhlemeier et al. (1989) Plant Cell 1:471. Laboratory, New York.
Lawrence et al. (1995) Plant Cell 7:1195.
Marcotte et al. (1989) Plant Cell 1:969.
Martin et al. (1993) Science 262:1432.
Needleman and Wunsch (1970) J Mol. Biol. 48:443.
Odel et al (1985) Nature 313:810.
Olszewski (1988) Nucl. Acids. Res. 16:10765–10783.
Opperman et al. (1993) Science 263:221–223.
Ori et al. (1997) Plant Cell 9:521–532.
Parker et al. (1997) Plant Cell 9:879–894.
Pearson and Lipman (1988) Proc. Natl. Acad. Sci. USA 85:2444.
Pearson et al. (1994) Methods in Molecular Biology 24, 307–31.
Roshal et al. (1987) EMBO J. 6:1155.
Ryals et al. (1994) Plant Physiol. 104:1109–1112.
Ryals et al. (1996) Plant Cell 8:1809–1819.
Sambrook et al. (1989) In Molecular Cloning: A Laboratory Manual, Cold Spring Harbor, New York.
Schaffner& Sheen (1991) Plant Cell 3:997.
Schemthaner et al. (1988) EMBO J. 7:1249.
Siebertz et al. (1989) Plant Cell 1:961.
Smith and Waterman (1981) Adv. Appl. Math. 2:482.
Smith et al. (1985) Science 229:1219–1224.
Song et al. (1995) Science 270:1804.
Stockhause et al. (1997) The Plant Cell 9:479–489.
Takahashi (1956) Phytopathology 46:654–656.
Takahashi et al. (1994) The Plant Journal 6:369–377.
Terada & Shimamoto (1990) Mol. Gen. Genet. 220:389.
Uknes et al. (1992) Plant Cell 4:645–656.
Ward et al. (1991) Plant Cell 3:1085–1094.
Weissbach & Weissbach (1989) Methods for Plant Molecular Biology, Academic Press.
Whitham et al. (1994) Cell 78:1101–1115.
Yamamoto et al. (1991) Plant Cell 3:371–82.

That which is claimed:

1. A transgenic plant comprising:
   (a) a first nucleic acid molecule encoding one or more protein products of the N gene, wherein said N gene confers resistance to a phytopathogen in a plant; and
   (b) a second nucleic acid molecule comprising a transgene, said transgene comprising a heterologous promoter operably linked to a coding sequence encoding a protein consisting of the TIR domain of the N protein;
   wherein co-expression of the first and second nucleic acid molecules produces a constitutive systemic acquired resistance response in the plant.

2. The plant of claim 1, wherein the first nucleic acid molecule is expressed under control of the native N gene promoter.

3. The plant of claim 1, wherein the first nucleic acid molecule encodes an N protein or an N-tr protein.

4. Transgenic seed of the plant of claim 1, wherein said seed comprise said first and said second nucleic acid mol 5. A method of producing a plant that exhibits an SAR response in the absence of pathogen infection, wherein the method comprises introducing a transgene into a plant having an N gene, wherein said N gene confers resistance to a phytopathogen, wherein said transgene comprises a heterologous promoter operably linked to a coding sequence encoding a a protein consisting essentially of the TIR domain of the N protein, and wherein co-expression of the N gene and the TIR domain produces a SAR response in the plant.

6. A plant produced by the method of claim 5.

7. Transgenic seed of the plant of claim 6, wherein said seed comprise said transgene and the N gene.

8. A transgenic plant comprising:
- (a) a first nucleic acid molecule encoding an N gene product having a TIR domain, wherein said first nucleic acid molecule confers resistance to a phytopathogen in a plant; and
- (b) a second nucleic acid molecule comprising a transgene, said transgene comprising a heterologous promoter operably linked to a coding sequence encoding a polypeptide consisting essentially of said TIR domain;

wherein co-expression of the first and second nucleic acid molecules produces a constitutive SAR response in the plant.

9. A transgenic plant comprising:
- (a) a first nucleic acid molecule encoding an N protein and an N-tr protein, wherein said first nucleic acid molecule confers resistance to a phytopathogen in a plant; and
- (b) a second nucleic acid molecule comprising a transgene, said transgene comprising a heterologous promoter operably linked to a coding sequence encoding a polypeptide consisting essentially of an N protein TIR domain;

wherein expression of the first and second nucleic acid molecules produces increased resistance to at least one phytopathogen.

10. The plant of claim 9, wherein the first nucleic acid molecule is a native nucleic acid molecule.

11. The plant of claim 10, wherein the first nucleic acid molecule is a native N gene.

12. The plant of claim 9, wherein the N protein comprises the amino acid sequence as shown in SEQ ID NO:3.

13. The plant of claim 9, wherein the N-tr protein comprises the amino acid sequence as shown in SEQ ID NO:5.

14. The plant of claim 13, wherein the plant is selected from the group consisting of tobacco, tomato and pepper.

15. Transgenic seed of the plant of claim 9, wherein said seed comprise said first and said second nucleic acid molecules.

16. A method for increasing the disease resistance of a plant, wherein said method comprises:
- (a) obtaining a plant comprising a first nucleic acid molecule encoding one or more protein products of the N gene wherein said N gene confers resistance to a phytopathogen in a plant; and
- (b) introducing into the genome of said plant a second nucleic acid molecule comprising a transgene, said transgene comprising a heterologous promoter operably linked to a coding sequence encoding a protein consisting essentially of the TIR domain of the N protein;

wherein co-expression of the first and second nucleic acid molecules produces a constitutive systemic acquired resistance response in the plant.

17. A plant produced by the method of claim 16, wherein the first nucleic acid molecule is a native nucleic acid molecule.

18. A plant produced by the method of claim 16, wherein said plant comprising said first nucleic acid molecule has been transformed with said nucleic acid molecule.

* * * * *